US012797007B2

(12) United States Patent
Lee et al.

(10) Patent No.: US 12,797,007 B2
(45) Date of Patent: Nov. 17, 2026

(54) CONTACTLESS RESPIRATION GUIDANCE SYSTEM FACILITATING REAL-TIME FEEDBACK

(71) Applicant: Google LLC, Mountain View, CA (US)

(72) Inventors: Reena Singhal Lee, Menlo Park, CA (US); Defne Gurel, London (GB); Dongeek Shin, San Jose, CA (US)

(73) Assignee: GOOGLE LLC, Mountain View, CA (US)

( * ) Notice: Subject to any disclaimer, the term of this patent is extended or adjusted under 35 U.S.C. 154(b) by 150 days.

(21) Appl. No.: 18/834,459

(22) PCT Filed: Feb. 1, 2022

(86) PCT No.: PCT/US2022/014701
§ 371 (c)(1),
(2) Date: Jul. 30, 2024

(87) PCT Pub. No.: WO2023/149861
PCT Pub. Date: Aug. 10, 2023

(65) Prior Publication Data

US 2025/0169754 A1 May 29, 2025

(51) Int. Cl.
*A61B 5/00* (2006.01)
*A61B 5/08* (2006.01)

(52) U.S. Cl.
CPC ............ *A61B 5/486* (2013.01); *A61B 5/0816* (2013.01); *A61B 5/4836* (2013.01); *A61B 5/7221* (2013.01)

(58) Field of Classification Search
CPC ..... A61B 5/486; A61B 5/0816; A61B 5/4836; A61B 5/7221
(Continued)

(56) References Cited

U.S. PATENT DOCUMENTS 10,058,290 B1 8/2018 Proud
10,064,570 B2 * 9/2018 Stone .................. A61B 5/6831
(Continued)

FOREIGN PATENT DOCUMENTS

JP 2021/078989 5/2021
KR 101780781 9/2017
(Continued)

OTHER PUBLICATIONS

International Preliminary Report on Patentability for PCT/US2021/014701, mailed on Aug. 8, 2024, 8 pages.
(Continued)

*Primary Examiner* — Michael Tomaszewski
(74) *Attorney, Agent, or Firm* — DORITY & MANNING P.A.

(57) ABSTRACT

Systems and methods for closed-loop, contactless respiration guidance providing quantified alignment feedback data in real-time are provided. In one embodiment, a computer-implemented method can include receiving, by a computing system operatively coupled to one or more processors, input data including respiration data indicative of an entity's respiration. The computer-implemented method can include converting, by the computing system, the respiration data into an entity respiration signal such that the entity respiration signal tracks the entity's respiration in real-time. The computer-implemented method can include comparing, by the computing system, the entity respiration signal to a suggested respiration signal indicative of a suggested respiration. The computer-implemented method can include providing, by the computing system, alignment feedback data to the entity in real-time based at least in part on the entity's respiration. The alignment feedback data can be indicative of alignment of the entity respiration signal with the suggested respiration signal.

20 Claims, 10 Drawing Sheets

(58) Field of Classification Search
USPC .......................................................... 600/301
See application file for complete search history.

(56) References Cited

U.S. PATENT DOCUMENTS

| | | | | |
|---|---|---|---|---|
| 10,369,310 | B2 * | 8/2019 | Ramanan | A61M 16/0069 |
| 10,506,969 | B2 * | 12/2019 | Yadollahi | A61B 5/11 |
| 11,191,448 | B2 * | 12/2021 | Mankodi | A61M 21/02 |
| 11,517,256 | B2 * | 12/2022 | Den Brinker | A61B 7/003 |
| 2004/0097823 | A1 * | 5/2004 | Friedrichs | A61B 5/08 600/534 |
| 2006/0020221 | A1 * | 1/2006 | Silpachai | A61B 5/097 600/529 |
| 2006/0106289 | A1 * | 5/2006 | Elser | A01K 29/005 600/300 |
| 2006/0212273 | A1 * | 9/2006 | Krausman | A61B 5/4818 702/189 |
| 2008/0064965 | A1 * | 3/2008 | Jay | A61B 5/02028 600/529 |
| 2010/0268093 | A1 * | 10/2010 | Balji | A61B 5/0205 600/484 |
| 2012/0119115 | A1 | 5/2012 | Iwata | |
| 2014/0343448 | A1 * | 11/2014 | Russell | A61B 5/0002 600/536 |
| 2014/0350361 | A1 | 11/2014 | Chazal et al. | |
| 2015/0208964 | A1 * | 7/2015 | Addison | A61B 5/14551 600/324 |
| 2015/0223733 | A1 | 8/2015 | Al-Alusi | |
| 2015/0250963 | A1 * | 9/2015 | Ramanan | A61M 16/0069 128/204.23 |
| 2016/0345862 | A1 * | 12/2016 | Li | A61B 5/0816 |
| 2017/0119303 | A1 * | 5/2017 | Yadollahi | A61B 5/11 |
| 2017/0150902 | A1 * | 6/2017 | Gay | A61B 5/0816 |
| 2017/0296127 | A1 * | 10/2017 | Takala | A61B 5/086 |
| 2019/0133479 | A1 * | 5/2019 | Chang | A61B 5/0816 |
| 2020/0163586 | A1 * | 5/2020 | Mccann | A61B 5/0816 |
| 2020/0215383 | A1 * | 7/2020 | Mankodi | A61B 5/0816 |
| 2021/0090309 | A1 | 3/2021 | Gough et al. | |
| 2021/0150873 | A1 | 5/2021 | Shouldice et al. | |
| 2022/0007965 | A1 * | 1/2022 | Tiron | A61B 5/0823 |
| 2022/0058971 | A1 * | 2/2022 | Mankodi | A61B 5/7455 |
| 2023/0301545 | A1 * | 9/2023 | Park | A61B 5/086 |
| 2025/0169754 | A1 * | 5/2025 | Lee | A61B 5/0816 |

FOREIGN PATENT DOCUMENTS

| | | | | |
|---|---|---|---|---|
| WO | WO 2020146259 | | 7/2020 | |
| WO | WO-2020146259 | A1 * | 7/2020 | A63B 71/0622 |

OTHER PUBLICATIONS

International Preliminary Report on Patentability for PCT/US2022/014701, mailed on Aug. 15, 2024, 9 pages.

International Search Report and Written Opinion for PCT/US2022/014701, mailed on Sep. 12, 2022, 13 pages.

Alizadeh et al., "Remote Monitoring of Human Vital Signs Using mm-Wave FMCW Radar", Institute of Electrical and Electronics Engineers Access, vol. 7, 2019, 11 pages.

* cited by examiner

CONTACTLESS RESPIRATION GUIDANCE SYSTEM FACILITATING REAL-TIME FEEDBACK

PRIORITY CLAIM

This application is based upon and claims the right of priority under 35 U.S.C. § 371 to International Application No. PCT/US2022/014701 filed on Feb. 1, 2022. Applicant claims priority to and the benefit of each of such applications and incorporates all such applications herein by reference in their entirety.

FIELD

The present disclosure relates generally to guided breathing systems. More specifically, the present disclosure relates to closed-loop, contactless guided breathing systems that provide real-time feedback.

BACKGROUND

Guided breathing systems provide respiration exercises that can include a suggested breathing pattern that an entity can attempt to mimic. For example, such systems can monitor an entity's respiration, output a suggested breathing pattern, and/or provide feedback related to the entity's respiration. The feedback can include biometric feedback that can be indicative of, for instance, the entity's breathing rate, heart rate, and/or movement.

SUMMARY

Aspects and advantages of embodiments of the present disclosure will be set forth in part in the following description, or can be learned from the description, or can be learned through practice of the embodiments.

According to an example embodiment, a computing system can include one or more processors and one or more non-transitory computer-readable storage media that store instructions that, when executed by the one or more processors, cause the computing system to perform operations. The operations can include: receiving input data including respiration data indicative of an entity's respiration; converting the respiration data into an entity respiration signal such that the entity respiration signal tracks the entity's respiration in real-time; comparing the entity respiration signal to a suggested respiration signal indicative of a suggested respiration; and/or providing alignment feedback data to the entity in real-time based at least in part on the entity's respiration. The alignment feedback data can be indicative of alignment of the entity respiration signal with the suggested respiration signal.

According to another example embodiment, a computer-implemented method can include: receiving, by a computing system operatively coupled to one or more processors, input data including respiration data indicative of an entity's respiration; converting, by the computing system, the respiration data into an entity respiration signal such that the entity respiration signal tracks the entity's respiration in real-time; comparing, by the computing system, the entity respiration signal to a suggested respiration signal indicative of a suggested respiration; and/or providing, by the computing system, alignment feedback data to the entity in real-time based at least in part on the entity's respiration. The alignment feedback data can be indicative of alignment of the entity respiration signal with the suggested respiration signal.

According to another example embodiment, a computing system can include one or more processors and one or more non-transitory computer-readable storage media that store instructions that, when executed by the one or more processors, cause the computing system to perform operations. The operations can include receiving a continuous chirp radar signal including respiration data indicative of an entity's respiration. The continuous chirp radar signal can include a plurality of chirps. The operations can further include converting the continuous chirp radar signal into an entity respiration amplitude signal such that the entity respiration amplitude signal tracks the entity's respiration in real-time. The signal amplitude of the entity respiration amplitude signal can be generated upon receipt of each of the plurality of chirps. The operations can further include comparing the entity respiration amplitude signal to a suggested respiration signal indicative of a suggested respiration. The operations can further include providing alignment feedback data to the entity in real-time based at least in part on the entity's respiration. The alignment feedback data can be indicative of alignment of the entity respiration amplitude signal with the suggested respiration signal.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which.

DETAILED DESCRIPTION

Figure 1:
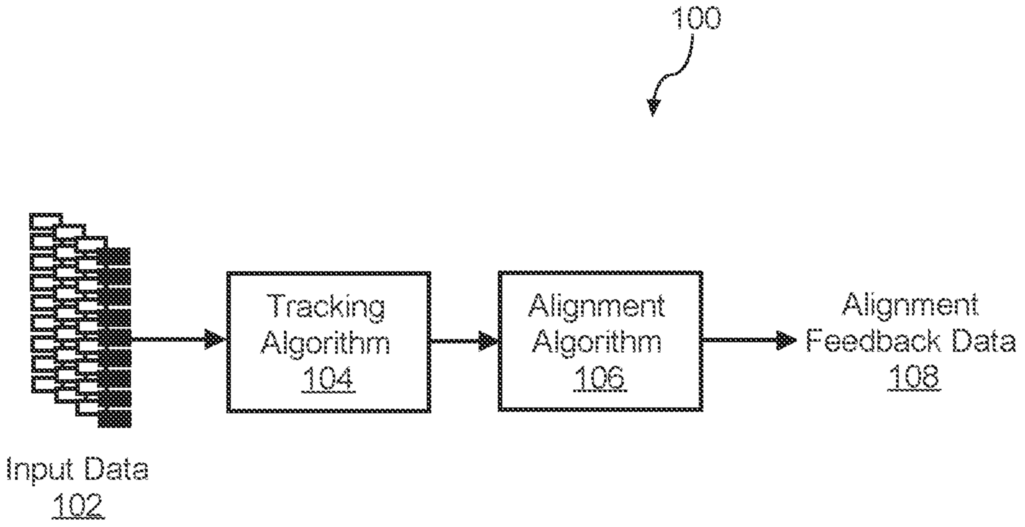
FIGS. 1, 2, 3, and 4 each illustrate a data flow diagram of an example, non-limiting data flow process according to one or more example embodiments of the present disclosure.

Reference now will be made in detail to embodiments of the present disclosure, one or more examples of which are illustrated in the drawings. Each example is provided by way of explanation of the present disclosure, not limitation of the present disclosure. In fact, it will be apparent to those skilled in the art that various modifications and variations can be made in the present disclosure without departing from the scope or spirit of the disclosure. For instance, features illustrated or described as part of one embodiment can be used with another embodiment to yield a still further embodiment. Thus, it is intended that the present invention covers such modifications and variations as come within the scope of the appended claims and their equivalents.

As referenced herein, the term "entity" refers to a human, a user, an end-user, a consumer, and/or another type of entity that can implement one or more embodiments of the present disclosure as described herein, illustrated in the accompanying drawings, and/or included in the appended claims. As referenced herein, the terms "or" and "and/or" are generally intended to be inclusive, that is (i.e.), "A or B" or "A and/or B" are each intended to mean "A or B or both." As referred to herein, the terms "first," "second," "third," etc. can be used interchangeably to distinguish one component or entity from another and are not intended to signify location, functionality, or importance of the individual components or entities. As used herein, the use of the term "about" and/or "approximate" in conjunction with a numerical value refers to within 10% of the indicated numerical value. As referenced herein, the terms "couple," "couples," "coupled," and/or "coupling" refer to chemical coupling (e.g., chemical bonding), communicative coupling, electrical and/or electromagnetic coupling (e.g., capacitive coupling, inductive coupling, direct and/or connected coupling, etc.), mechanical coupling, operative coupling, optical coupling, and/or physical coupling.

Example aspects of the present disclosure are directed to a closed-loop, contactless respiration guidance system that can provide quantified alignment feedback in real-time to an entity (e.g., a human) attempting to mimic a suggested respiration (e.g., a suggested breathing pattern) recommended by the system. The quantified alignment feedback can be indicative of the degree to which the entity's respiration is aligned with the suggested respiration. As referenced herein, "closed-loop" respiration guidance system can describe a system that can, for example: receive first input data indicative of the entity's respiration at a first time ($T_1$); provide the entity with a first suggested respiration based at least in part on the first input data; receive second input data indicative of the entity's respiration while the entity is attempting to mimic (e.g., simulate) the first suggested respiration at a second time ($T_2$) that is after (e.g., subsequent to) the first time ($T_1$); and/or provide the entity with a second suggested respiration based at least in part on the second input data. In some embodiments, such a closed-loop process can continue indefinitely while the entity is implementing the disclosed technology according to one or more embodiments described herein.

According to one or more example embodiments of the present disclosure, a computing system described herein can facilitate contactless respiration guidance with quantified alignment feedback in real-time. For example, to facilitate such contactless respiration guidance with quantified alignment feedback in real-time, the computing system according to example embodiments described herein can perform operations that can include, but are not limited to: receiving input data that can include and/or constitute respiration data indicative of an entity's respiration; converting the respiration data into an entity respiration signal such that the entity respiration signal tracks the entity's respiration in real-time; comparing the entity respiration signal to a suggested respiration signal indicative of a suggested respiration; and/or providing alignment feedback data to the entity in real-time based at least in part on the entity's respiration. In some embodiments, the alignment feedback data can be indicative of alignment of the entity respiration signal with the suggested respiration signal. For example, as described in further detail below, in example embodiments described herein, the alignment feedback data can be generated based on comparing the entity respiration signal to a suggested respiration signal that can be indicative of a suggested respiration. For instance, in some embodiments, the alignment feedback data can be associated with a difference between the entity respiration signal and the suggested respiration signal. In at least one embodiment, the alignment feedback data can be associated with, for example, a difference of the amplitudes, frequencies, and/or phase of the entity respiration signal and the suggested respiration signal.

To perform the operations described above and/or other operations described herein, the computing system according to example embodiments of the present disclosure can include, be coupled to (e.g., communicatively, operatively, etc.), and/or otherwise be associated with one or more processors and/or one or more non-transitory computer-readable storage media. In these or other example embodiments, the one or more non-transitory computer-readable storage media can store instructions that, when executed by the one or more processors, can cause the computing system (e.g., via the one or more processors) to perform the operations described above and/or other operations described herein to facilitate contactless respiration guidance with quantified alignment feedback in real-time.

In accordance with one or more example embodiments of the present disclosure, the computing system can receive input data that can include and/or constitute respiration data that can be indicative of an entity's respiration (e.g., indicative of an entity's current, real-time breathing pattern). In at least one embodiment, such input data and/or respiration data can include and/or constitute, for instance, radar data indicative of the entity's respiration, high frequency radar data indicative of the entity's respiration, sonar data indicative of the entity's respiration, sound data indicative of the entity's respiration, video data indicative of the entity's respiration, time series data indicative of the entity's respiration, and/or other input data and/or respiration data that can be indicative of the entity's respiration.

In some embodiments, the computing system can receive a combination of different types of input data that can each include and/or constitute a certain type of respiration data that can be indicative of the entity's respiration. For example, in these or other embodiments, the computing system can receive radar data indicative of the entity's respiration, sonar data indicative of the entity's respiration, and video data indicative of the entity's respiration.

In one embodiment, the computing system can receive input data in the form of, for instance, a continuous chirp radar signal (e.g., a frequency-modulated continuous-wave (FMCW) radar signal) that can include and/or constitute respiration data that can be indicative of an entity's respiration. In this or another embodiment, the continuous chirp radar signal can include and/or constitute a plurality of chirps.

In one or more example embodiments, the computing system can receive the above-described input data and/or respiration data from one or more contactless sources and/or devices that can be included with, coupled to (e.g., communicatively, operatively, etc.), and/or otherwise associated with the computing system. In at least one embodiment, such one or more contactless sources and/or devices can capture, collect, and/or otherwise obtain such input data and/or respiration data without physically engaging the entity (e.g., without touching the entity). For instance, in one or more embodiments, the computing system can receive such input data and/or respiration data from one or more contactless sources and/or devices that can include, but are not limited to, a radar device (e.g., a high frequency radar, a real-time motion tracking radar, etc.), a sonar device, a camera device, an audio device (e.g., a microphone, etc.), and/or another contactless source and/or device that can capture, collect, and/or otherwise obtain such input data and/or respiration data without physically engaging the entity. In at least one embodiment, the computing system can receive the above-described continuous chirp radar signal from a high frequency radar (e.g., an FMCW radar) and/or a real-time motion tracking radar.

In at least one embodiment of the present disclosure, based at least in part on (e.g., in response to) receiving the above-described input data and/or respiration data, the computing system can convert the respiration data into an entity respiration signal such that the entity respiration signal can track the entity's respiration in real-time. For example, in some embodiments, upon receiving the input data and/or respiration data (e.g., immediately upon receiving the input data and/or respiration data, in real-time), the computing system can implement (e.g., execute, run, etc.) a tracking algorithm such as, for instance, a phase tracking algorithm having relatively low latency to convert the respiration data into an entity respiration amplitude signal such that the entity respiration amplitude signal can track (e.g., mimic, simulate, replicate, etc.) and/or be in sync with the entity's respiration in real-time (e.g., live, concurrently, and/or simultaneously with the entity's respiration).

As referenced herein, "relatively low latency" of the above-described phase tracking algorithm can refer to: latency that is lower (e.g., less) than the latency of other phase tracking algorithms; latency that is defined as being low according to a standard and/or a protocol associated with the technical field of signal processing; latency that is considered to be low by one having ordinary skill in the technical field of signal processing; latency that is unnoticeable by an entity as defined herein (e.g., unnoticeable by a human); latency that is low enough to allow for an entity as defined herein (e.g., a human) to perceive the above-described conversion of the respiration data into the entity respiration signal as occurring in real-time (e.g., live, instantaneously, etc.); and/or latency that is less than a defined amount of time (e.g., less than approximately 5 seconds, less than approximately 1 second, less than approximately 500 milliseconds (ms), less than approximately 100 ms, less than approximately 10 ms, etc.).

In one or more embodiments where the computing system receives the input data and/or respiration data in the form of a continuous chirp radar signal as described above (e.g., in the form of an FMCW radar signal that can be provided by a high frequency radar, an FMCW radar, a real-time motion tracking radar, etc.), the computing system can convert the continuous chirp radar signal into an entity respiration amplitude signal such that the entity respiration amplitude signal can track the entity's respiration in real-time. In these one or more embodiments, the signal amplitude of the entity respiration amplitude signal can be generated (e.g., by the computing system) upon receipt of each of the plurality of chirps. For example, in these or other embodiments, upon receiving the continuous chirp radar signal (e.g., immediately upon receiving the continuous chirp radar signal, in real-time), the computing system can implement (e.g., execute, run, etc.) the above-described phase tracking algorithm having relatively low latency to convert the continuous chirp radar signal into an entity respiration amplitude signal such that the entity respiration amplitude signal can track (e.g., mimic, simulate, replicate, etc.) and/or be in sync with the entity's respiration in real-time (e.g., live, concurrently, and/or simultaneously with the entity's respiration).

To facilitate the above-described conversion of the continuous chirp radar signal to such an entity respiration amplitude signal according to one or more embodiments, upon receiving the plurality of chirps of the continuous chirp radar signal (e.g., immediately upon receiving the plurality of chirps of the continuous chirp radar signal, in real-time), the computing system can implement (e.g., execute, run, etc.) the above-described phase tracking algorithm having relatively low latency to generate the signal amplitude of the entity respiration amplitude signal. For instance, in one embodiment, upon receiving a new chirp of the plurality of chirps (e.g., immediately upon receiving, in real-time, a chirp not previously received), the computing system can implement the phase tracking algorithm having relatively low latency to generate a new local amplitude of the entity respiration amplitude signal (e.g., a local amplitude not previously generated). In this embodiment, the new local amplitude can correspond to the new chirp. In this manner, the computing system according to example embodiments can thereby convert each chirp of the plurality of chirps, and thus the continuous chirp radar signal, into an entity respiration amplitude signal that can track (e.g., mimic, simulate, replicate, etc.) and/or be in sync with the entity's respiration in real-time (e.g., live, concurrently, and/or simultaneously with the entity's respiration).

To further facilitate the above-described conversion of the continuous chirp radar signal to such an entity respiration amplitude signal according to at least one embodiment of the present disclosure, upon receiving the continuous chirp radar signal (e.g., immediately upon receiving the continuous chirp radar signal, in real-time), the computing system can implement (e.g., execute, run, etc.) the above-described phase tracking algorithm having relatively low latency to perform one or more of the following operations.

In one embodiment, the computing system can implement the phase tracking algorithm having relatively low latency to remove noise data from the continuous chirp radar signal (e.g., using an exponential filter and/or an exponential smoothing process). In this embodiment, the noise data can include and/or constitute data that can be indicative of at least one movement corresponding to one or more second entities (e.g., movements of objects and/or other people).

In one embodiment, the computing system can implement the phase tracking algorithm having relatively low latency to map out a range that can be associated with the continuous chirp radar signal (e.g., using an exponential filter and/or an exponential smoothing process). In this embodiment, the range can include and/or constitute at least a portion of the entity's respiration data. In some embodiments, the range can include and/or constitute a spatial range that can be associated with and/or proximate to the entity. For example, in some embodiments, the range can be defined as a distance that extends between the entity and a radar device that captures, collects, and/or otherwise obtains the entity's respiration data. For instance, in at least one embodiment, the range can be defined as a distance that extends from, for example, the entity's chest to the radar device. In one embodiment, the range can be defined as a distance of approximately one (1) meter (m) extending between the entity's chest to the radar device. In at least one embodiment, the range can include one or more range bins that can include and/or constitute at least a portion of the entity's respiration data. For example, in one embodiment, the one or more range bins can be defined as distance intervals along the above-described range. For instance, in this or another embodiment, each of the one or more range bins can be defined as a distance of approximately three (3) centimeters (cm) that extend along a 1 m range between the entity's chest and the radar.

In one embodiment, the computing system can implement the phase tracking algorithm having relatively low latency to normalize the range into a range probability map that can include and/or constitute multiple range bins (e.g., the above-described one or more range bins). In this embodiment, each of the multiple range bins can include and/or constitute at least a portion of the respiration data. As referenced herein, a "range probability map" can constitute a vector that divides each of the range bin values with the sum all the range bin values (e.g., range_map/sum (range_map)).

In one embodiment, the computing system can implement the phase tracking algorithm having relatively low latency to apply one or more inertia functions to the range probability map and/or the multiple range bins to determine a center-of-mass that can correspond to the range probability map and/or the multiple range bins. In an embodiment, the computing system can implement the phase tracking algorithm to apply inertia as an element-wise low-pass filter. In this or another embodiment, as the range probability map gets updated over time, it should not change too frequently. In this or another embodiment, the effect of inertia can remove sudden motion artifacts. In this or another embodiment, the center-of-mass can constitute the expected value of the inertia-applied probability map. For instance, the center-of-mass can describe and/or constitute the range with the highest probability of describing the entity's chest region accurately. In some embodiments, the center-of-mass can constitute a range bin having the highest probability (e.g., compared to all other range bins) of accurately describing the entity's chest region and/or the entity's chest movements during respiration. In at least one embodiment, the computing system can implement the phase tracking algorithm to "lock" the phase values of the center-of-mass (e.g., to "lock" the phase values of such a particular range bin having the highest probability of accurately describing the entity's chest region and/or the entity's chest movements during respiration).

In one embodiment, the computing system can implement the phase tracking algorithm having relatively low latency to extract phase data that can correspond to the center-of-mass. In this embodiment, the phase data can be indicative of a wrapped phase signal that can correspond to the center-of-mass. It should be noted that, in some embodiments, the original range map can be computed from the continuous chirp radar signal by taking the absolute component of the fast Fourier transform (FFT). In some embodiments, the phase component of the FFT can be kept on the side (e.g., parked, saved, stored, etc.). In some embodiments, the range map dimension can be the same as the phase map dimension, since they come from the same FFT. In some embodiments, to extract phase data that can correspond to the center-of-mass, the computing system can implement the phase tracking algorithm having relatively low latency to extract (e.g., read) a particular phase value at the corresponding highest-user-chest-probability range bin identified in the previous step as described above.

In one embodiment, the computing system can implement the phase tracking algorithm having relatively low latency to perform a signal phase unwrapping process on the phase data and/or the wrapped phase signal to obtain a continuous phase signal that can correspond to the center-of-mass (e.g., an unwrapped phase signal that can correspond to the center-of-mass). In some embodiments, when computing phase per chirp, the phase value will be between negative pi (−pi or −¶) and positive pi (+pi or +¶). In some embodiments, over time, the phase value will oscillate within this range (e.g., within −pi (−¶) and +pi (+¶)) based on the entity's breathing frequency. However, in some embodiments, there can be an effect of "wrapping" when, for example, the phase value is pi−0.1 (¶−0.1) and the entity breathes in deep and the phase value increases it should bounce down to −pi (−¶), because the phase value cannot express a value greater than +pi (+¶). Thus, in some embodiments, the nature of "smoothness" of entity breathing can be exploited (e.g., leveraged), and whenever there is this sudden bounce from −pi (−¶) to pi (¶) or pi (¶) to −pi (−¶), it can be interpreted as a wrapping behavior and the ends can be "stitched" together to reconstruct the smooth breathing signal. For example, in at least one embodiment, the phase tracking algorithm having relatively low latency can implement a phase unwrapping algorithm such as, for instance, Itoh's phase unwrapping algorithm to perform the above-described signal phase unwrapping process on a one-dimensional (1-dimensional) phase time series that can be obtained from the previous step described above.

In one embodiment, the computing system can implement the phase tracking algorithm having relatively low latency to apply a filter to the continuous phase signal to obtain the entity respiration amplitude signal. In this embodiment, the filter can be operable to remove data that can be indicative of defined entity movements that can be associated with the entity's respiration (e.g., subtle movements the entity makes while inhaling and/or exhaling).

In accordance with at least one embodiment described herein, based at least in part on (e.g., in response to) converting the above-described respiration data and/or continuous chirp radar signal into the above-described entity respiration signal and/or entity respiration amplitude signal, the computing system can compare the entity respiration signal and/or entity respiration amplitude signal to a suggested respiration signal that can be indicative of a suggested respiration (e.g., a suggested breathing pattern that can be defined and/or recommended by the computing system). For instance, in one example embodiment, the computing system can compare the entity respiration signal and/or entity respiration amplitude signal to such a suggested respiration signal to determine the degree to which the entity respiration signal and/or entity respiration amplitude signal is aligned with the suggested respiration signal. In one example embodiment, the computing system can compare the entity respiration signal and/or entity respiration amplitude signal to a suggested respiration signal that can be generated by the computing system. In this or another example embodiment, such a suggested respiration signal can be indicative of a suggested respiration (e.g., a suggested breathing pattern) that can be defined and/or recommended by the computing system. In this or another example embodiment, the computing system can define and/or recommend such a suggested respiration and/or generate such a suggested respiration signal based at least in part on, for instance, one or more attributes and/or biometrics that can correspond to the entity (e.g., the entity's age, weight, height, real-time heart rate and/or average heart rate, real-time blood pressure and/or average blood pressure, etc.).

To facilitate the above-described comparison of the entity respiration signal and/or entity respiration amplitude signal to the suggested respiration signal and/or to determine the degree to which the entity respiration signal and/or entity respiration amplitude signal is aligned with the suggested respiration signal, the computing system according to example embodiments can implement (e.g., execute, run, etc.) an alignment algorithm. For example, in at least one embodiment, the computing system can implement an alignment algorithm that can apply a spectral similarity process to compare the entity respiration signal and/or entity respiration amplitude signal to a suggested respiration signal and/or determine the degree to which the entity respiration signal and/or entity respiration amplitude signal is aligned with the suggested respiration signal. In this embodiment, the degree to which the entity respiration signal and/or entity respiration amplitude signal is aligned with the suggested respiration signal can be expressed as an alignment score that can range from, for instance, a value of approximately zero (0) to a value of approximately one (1). In this embodiment, a value of zero (0) can be indicative of a relatively poor alignment (e.g., no alignment) and/or a value of one (1) can be indicative of a relatively good alignment (e.g., complete alignment). In this manner, the computing system according to example embodiments described herein can determine an alignment score that can be indicative of the degree of the alignment of the entity respiration signal and/or entity respiration amplitude signal with the suggested respiration signal.

As referenced herein, in some embodiments, "alignment" of the entity respiration signal (e.g., the entity respiration amplitude signal) with the suggested respiration signal can occur when the entity respiration signal (e.g., the entity respiration amplitude signal) is visually and/or mathematically in phase or approximately in phase with the suggested respiration signal. As used herein, the "degree" of alignment of the entity respiration signal (e.g., the entity respiration amplitude signal) with the suggested respiration signal can describe, for example, visually and/or mathematically how close (or not) the entity respiration signal (e.g., the entity respiration amplitude signal) is to being in phase or approximately in phase with the suggested respiration signal.

To determine the above-described alignment score in accordance with at least one embodiment of the present disclosure, the computing system can implement (e.g., execute, run, etc.) the alignment algorithm described above to perform one or more of the following operations. For example, in one embodiment, the computing system can implement the alignment algorithm to: compute spectrum vectors of respiration data for phase invariance by computing a first spectrum vector that can correspond to the entity's respiration data and/or the entity respiration signal (e.g., the entity respiration amplitude signal) and computing a second spectrum vector that can correspond to suggested respiration data (e.g., data indicative of the suggested respiration that can be defined and/or recommended by the computing system as described above) and/or the suggested respiration signal; apply a normalization function such as, for instance, an L2-normalization function to the first spectrum vector and the second spectrum vector to compute a first L2-normalized spectrum vector and a second L2-normalized spectrum vector, respectively; compute the alignment score of the first and second L2-normalized spectrum vectors using a dot product operation; and/or apply a softmax function to the alignment score to improve dynamic range associated with the alignment score.

In one or more embodiments, the above-described spectrum vectors can each constitute an absolute FFT of a signal (e.g., an absolute FFT value corresponding to a phase signal, amplitude signal, etc.). For example, in one embodiment, the above-described first spectrum vector can constitute the absolute FFT (e.g., absolute FFT value) of the above-described continuous phase signal that can correspond to the center-of-mass (e.g., an unwrapped phase signal that can correspond to the center-of-mass) that can be obtained using a phase unwrapping algorithm as described above (e.g., using Itoh's phase unwrapping algorithm). In at least one embodiment, the above-described L2-normalization function can involve dividing each element of a spectrum vector with the L2-norm (=energy) of the whole vector (e.g., to obtain an L2-normalized vector). In one embodiment, the above-described dot product operation can involve taking a dot product of two (2) such normalized vectors (e.g., two (2) L2-normalized vectors), which can involve taking the element-wise product between the two vectors and summing them all up. In some embodiments, such a dot product will be maximized to one (1) if the two (2) normalized vectors are exactly the same. For example, the unnormalized vector can be expressed as: dot(a/||a||, a/||a||)=dot(a, a)/||a||^2=||a||^2/||a||^2=1, while the dot product will be minimized if the two (2) normalized vectors look different. Thus, in some embodiments, the dot product is a measure of similarity of the entity's respiration (e.g., the entity's breathing pattern) and the suggested respiration (e.g., the suggested breathing pattern). In some example embodiments of the present disclosure, the dot product and/or such a measure of similarity of the entity's respiration and the suggested respiration is described as the degree to which the entity's respiration is aligned with the suggested respiration.

In one or more embodiments described herein, the computing system can provide alignment feedback data to the entity in real-time based at least in part on the entity's respiration. In these one or more embodiments, the alignment feedback data can be indicative of alignment of the entity respiration signal and//or the entity respiration amplitude signal with the suggested respiration signal. For example, in these one or more embodiments, based at least in part on (e.g., in response to) receiving the above-described input data (e.g., the continuous chirp radar signal) that can include and/or constitute respiration data that can be indicative of the entity's respiration, the computing system can (e.g., immediately upon receipt of such input data, in real-time): implement the above-described phase tracking algorithm having relatively low latency to convert the respiration data into the entity respiration signal (e.g., the entity respiration amplitude signal); implement the above-described alignment algorithm to compare the entity respiration signal (e.g., the entity respiration amplitude signal) to the suggested respiration signal and/or determine the alignment score corresponding to such signals; and/or provide the alignment score and/or other alignment feedback data to the entity in real-time in response to the entity's respiration (e.g., live, concurrently, and/or simultaneously with the entity's respiration). In these one or more embodiments, the computing system can perform such operations in real-time while the entity is performing, for instance, a guided breathing exercise that can be defined and/or communicated to the entity by the computing system based on the above-described suggested respiration and/or suggested respiration signal that can be defined and/or generated by the computing system as described above. For instance, in these one or more embodiments, the computing system can perform such operations in real-time while the entity is attempting to align the entity's respiration with the suggested respiration and/or align the entity respiration signal (e.g., the entity respiration amplitude signal) with the suggested respiration signal.

In an additional and/or alternative embodiment of the present disclosure, the computing system can provide the entity with alignment feedback data that can include and/or constitute an alignment visualization that can include the entity respiration signal (e.g., the entity respiration amplitude signal) and/or the suggested respiration signal. For example, in this additional and/or alternative embodiment, the computing system can provide the entity with an alignment visualization that can include and/or constitute a visualization of the entity respiration signal (e.g., the entity respiration amplitude signal) overlayed on and/or proximate to the suggested respiration signal (e.g., superimposed on and/or adjacent to the suggested respiration signal). In one embodiment, such an alignment visualization can include and/or constitute an image (e.g., a static image) of the entity respiration signal (e.g., the entity respiration amplitude signal) overlayed on and/or proximate to the suggested respiration signal (e.g., superimposed on and/or adjacent to the suggested respiration signal). In another embodiment, such an alignment visualization can include and/or constitute a video (e.g., a live, real-time video) of the entity respiration signal (e.g., the entity respiration amplitude signal) overlayed on and/or proximate to the suggested respiration signal (e.g., superimposed on and/or adjacent to the suggested respiration signal).

In some embodiments, the computing system can provide the entity with one or more other types of alignment feedback data that can be indicative of alignment of the entity respiration signal with the suggested respiration signal. For example, in these or other embodiments, the computing system can provide the entity with such alignment feedback data in the form of, for instance: audio data (e.g., a digital voice, a buzzer, an audible alarm, etc.); text, numeric, and/or alphanumeric data (e.g., letters, numbers, words, a written message, a push notification, etc.); graphical data (e.g., a symbol, a character, an icon, an emoji, etc.); haptic data (e.g., vibration of a device associated with the entity such as, for instance, a smart phone, a wearable computing device, etc.); visual data (e.g., a light having intensity that is correlated with and/or varies in response to the degree of alignment), and/or another form of data. In these or other embodiments, the computing system can provide such one or more other types of alignment feedback data to the entity in real-time in response to the entity's respiration (e.g., live, concurrently, and/or simultaneously with the entity's respiration).

In at least one embodiment, the computing system can provide the above-described alignment feedback data to the entity over a network such as, for example, a local area network (LAN), a wireless and/or wired network, a wide area network (WAN), a personal area network (PAN), a wireless personal area network (WPAN), and/or another network. In this or another embodiment, the computing system can provide the alignment feedback data to the entity via, for instance: a monitor and/or screen that can be coupled to, included with, and/or otherwise associated with the computing system; a monitor and/or screen that can be coupled to, included with, and/or otherwise associated with a computing device that can be associated with the entity (e.g., a wearable computing device, a computer, a smart phone, a tablet, etc.); and/or another device.

Example aspects of the present disclosure provide several technical effects, benefits, and/or improvements in computing technology. For instance, by facilitating contactless respiration guidance with quantified alignment feedback in real-time according to example embodiments of the present disclosure, the computing system can thereby eliminate one or more contact-based components (e.g., devices, hardware, software, etc.) and/or processes (e.g., workflows) that would otherwise be used to obtain, capture, and/or collect an entity's respiration data. In another example, by implementing the above-described phase tracking algorithm having relative low latency (e.g., relative to other phase tracking algorithms) to convert the respiration data into the entity respiration signal (e.g., the entity respiration amplitude signal) as described above, the computing system according to example embodiments can thereby improve the processing speed, performance, and/or efficiency of one or more processors that can perform such a conversion. In this example, by improving the processing speed, performance, and/or efficiency of such one or more processors, the computing system can thereby reduce computational costs associated with such one or more processors. In another example, by comparing the entity respiration signal (e.g., the entity respiration amplitude signal) to the suggested respiration signal in real-time and/or providing the entity with the alignment feedback in real-time according to example embodiments of the present disclosure, the computing system can thereby eliminate the use of one or more memory devices to store the above-described input data and/or respiration data that can be indicative of the entity's respiration. In this example, by eliminating the use of one or more memory devices to store such data, the computing system according to example embodiments can thereby increase the available storage capacity of such one or more memory devices and/or reduce operational costs associated with such one or more memory devices.

FIG. 1 illustrates a data flow diagram of an example, non-limiting data flow process 100 according to one or more example embodiments of the present disclosure. A computing system described herein can implement data flow process 100 to facilitate a closed-loop, contactless respiration guidance process that provides quantified alignment feedback data in real-time in accordance with example embodiments of the present disclosure. For example, user computing device 710 and/or server component system 740 described below and illustrated in FIG. 7 can implement data flow process 100 to facilitate a closed-loop, contactless respiration guidance process that provides quantified alignment feedback data in real-time in accordance with example embodiments of the present disclosure.

As illustrated in the example embodiment depicted in FIG. 1, data flow process 100 can include inputting input data 102 into a tracking algorithm 104. In this embodiment, data flow process 100 can further include inputting the output of tracking algorithm 104 into an alignment algorithm 106 that can output alignment feedback data 108. In at least one embodiment, user computing device 710 and/or server component system 740 described below with reference to FIG. 7 can implement tracking algorithm 104 and/or alignment algorithm 106 to provide alignment feedback data 108 in real-time based at least in part on receiving input data 102.

Input data 102 can include and/or constitute respiration data (not illustrated) that can be indicative of an entity's respiration (e.g., indicative of an entity's current, real-time breathing pattern). For example, input data 102 can include and/or constitute radar data indicative of the entity's respiration, high frequency radar data indicative of the entity's respiration, sonar data indicative of the entity's respiration, sound data indicative of the entity's respiration, video data indicative of the entity's respiration, time series data indicative of the entity's respiration, and/or other data that can be indicative of the entity's respiration.

In some embodiments, input data 102 can include and/or constitute a combination of different types of input data that can each include and/or constitute a certain type of respiration data that can be indicative of the entity's respiration. For example, input data 102 can include and/or constitute a combination of, for instance, radar data indicative of the entity's respiration, sonar data indicative of the entity's respiration, and video data indicative of the entity's respiration.

In at least one embodiment, input data 102 can include and/or constitute a continuous chirp radar signal such as, for instance, a frequency-modulated continuous-wave (FMCW) radar signal that can include and/or constitute respiration data that can be indicative of an entity's respiration. In this or another embodiment, the continuous chirp radar signal and/or the FMCW radar signal can include and/or constitute a plurality of chirps.

In at least one embodiment, input data 102 and/or the above-described respiration data can be obtained from one or more contactless sources and/or devices that can capture, collect, and/or otherwise obtain input data 102 and/or the respiration data without physically engaging the entity (e.g., without touching the entity). For instance, input data 102 and/or the respiration data can be obtained from a radar device (e.g., a high frequency radar, a real-time motion tracking radar, etc.), a sonar device, a camera device, an audio device (e.g., a microphone, etc.), and/or another contactless source and/or device that can capture, collect, and/or otherwise obtain input data 102 and/or the respiration data without physically engaging the entity. In at least one embodiment where input data 102 includes and/or constitutes a continuous chirp radar signal as described above (e.g., an FMCW radar signal), such a continuous chirp radar signal can be obtained from a high frequency radar (e.g., an FMCW radar) and/or a real-time motion tracking radar.

Figure 2:
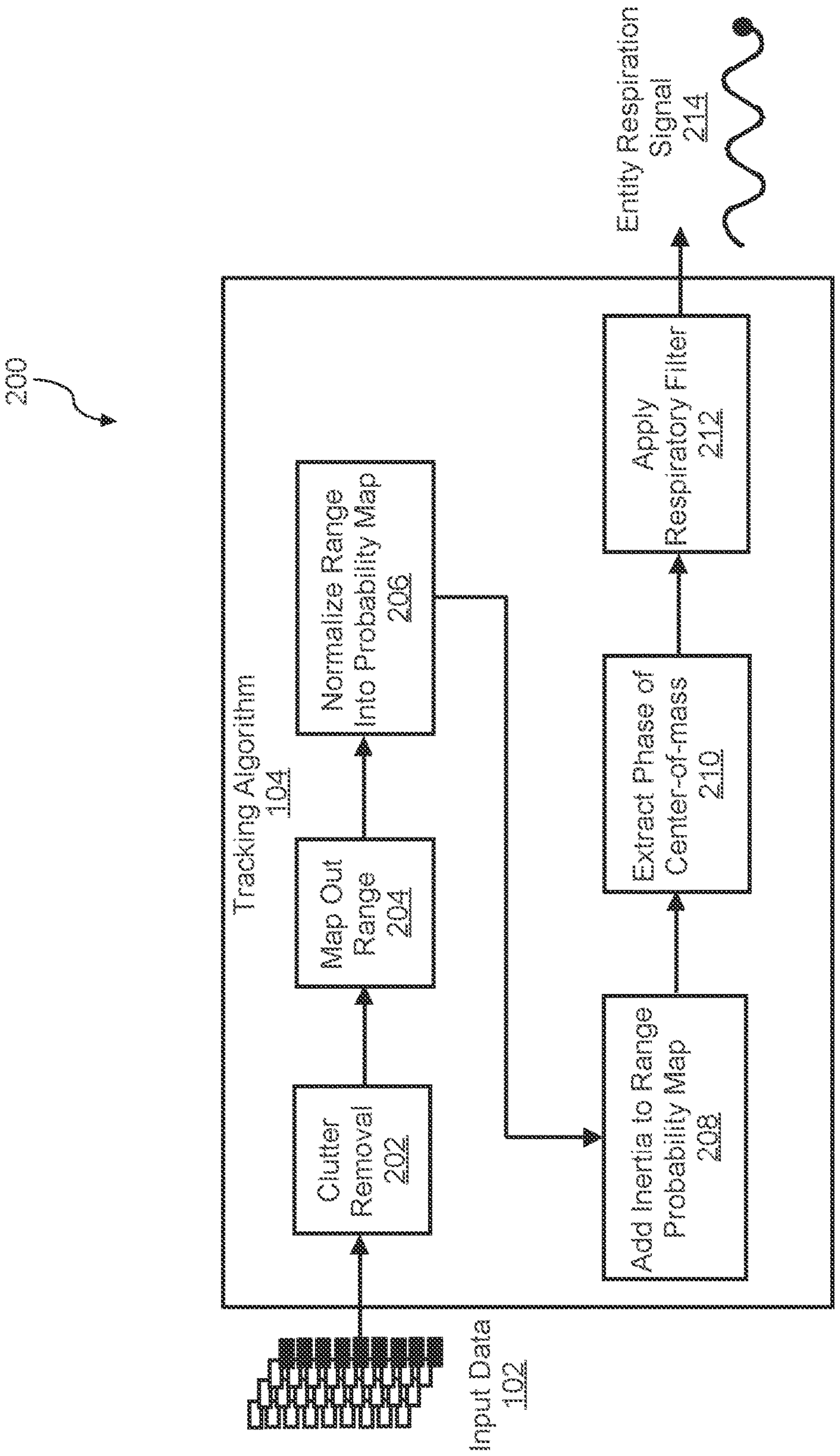

Tracking algorithm 104 can include and/or constitute a phase tracking algorithm having relatively low latency (e.g., relative to other phase tracking algorithms). In one embodiment, tracking algorithm 104 can convert the respiration data of input data 102 into an entity respiration signal such that the entity respiration signal can track (e.g., mimic, simulate, replicate, etc.) and/or be in sync with the entity's respiration in real-time (e.g., live, concurrently, and/or simultaneously with the entity's respiration). In another embodiment, tracking algorithm 104 can convert the respiration data of input data 102 into an entity respiration amplitude signal such that the entity respiration amplitude signal can track (e.g., mimic, simulate, replicate, etc.) and/or be in sync with the entity's respiration in real-time (e.g., live, concurrently, and/or simultaneously with the entity's respiration). Provided below with reference to the example embodiment depicted in FIG. 2 are details describing how tracking algorithm 104 can convert the respiration data of input data 102 into an entity respiration signal such that the entity respiration signal can track (e.g., mimic, simulate, replicate, etc.) and/or be in sync with the entity's respiration in real-time (e.g., live, concurrently, and/or simultaneously with the entity's respiration).

Figure 4:
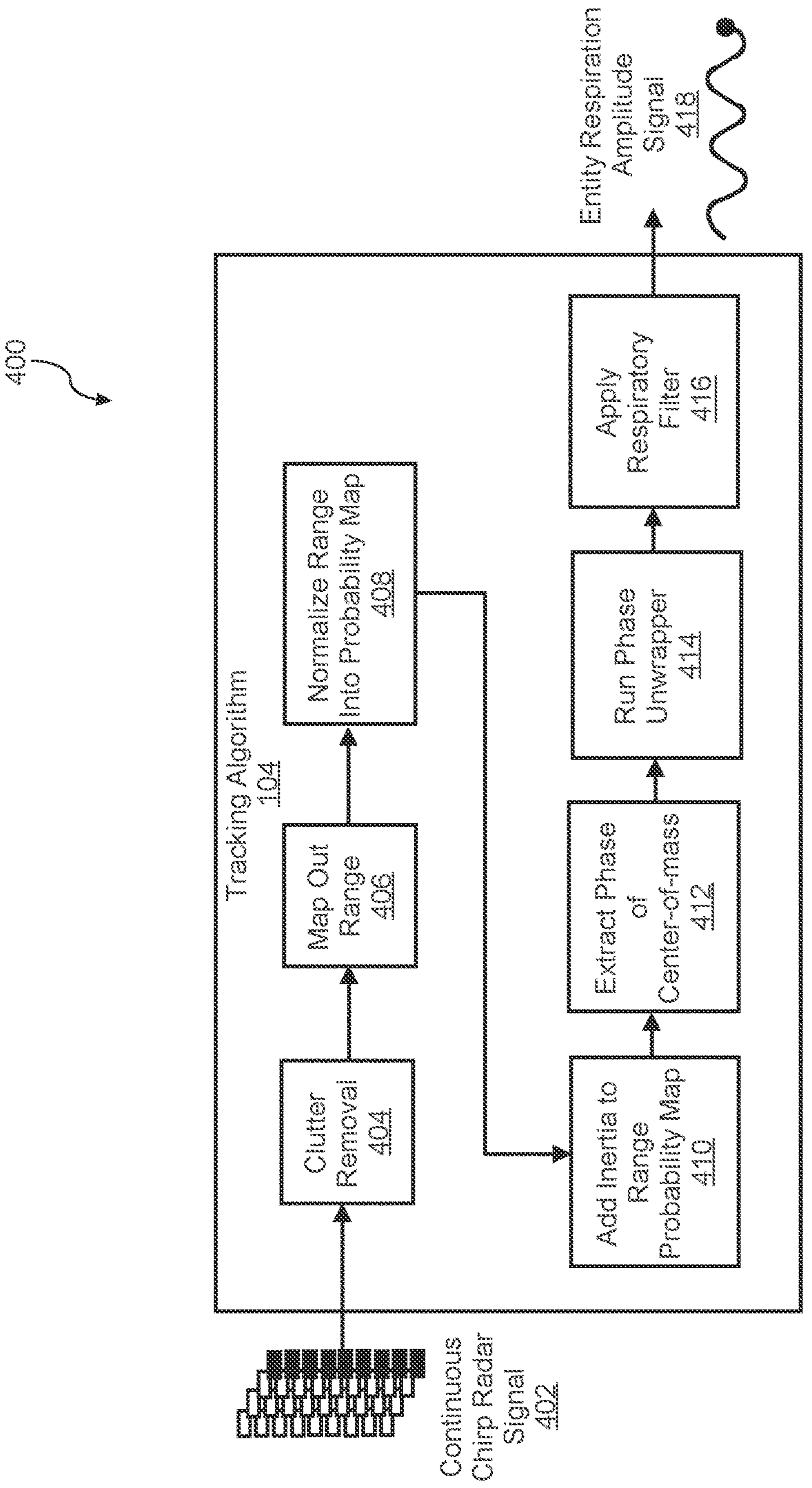

In an embodiment where input data 102 includes and/or constitutes a continuous chirp radar signal as described above (e.g., an FMCW radar signal), tracking algorithm 104 can convert the continuous chirp radar signal into an entity respiration amplitude signal such that the entity respiration amplitude signal can track (e.g., mimic, simulate, replicate, etc.) and/or be in sync with the entity's respiration in real-time (e.g., live, concurrently, and/or simultaneously with the entity's respiration). In this embodiment, tracking algorithm 104 can generate the signal amplitude of the entity respiration amplitude signal upon receipt of each of the plurality of chirps. For instance, upon receiving a new chirp of the plurality of chirps (e.g., immediately upon receiving, in real-time, a chirp not previously received), tracking algorithm 104 can generate a new local amplitude of the entity respiration amplitude signal (e.g., a local amplitude not previously generated). The new local amplitude can correspond to the new chirp. In this manner, tracking algorithm 104 can thereby convert each chirp of the plurality of chirps, and thus the continuous chirp radar signal, into an entity respiration amplitude signal that can track (e.g., mimic, simulate, replicate, etc.) and/or be in sync with the entity's respiration in real-time (e.g., live, concurrently, and/or simultaneously with the entity's respiration). Provided below with reference to the example embodiment depicted in FIG. 4 are further details describing how tracking algorithm 104 can convert the continuous chirp radar signal into an entity respiration amplitude signal such that the entity respiration amplitude signal can track (e.g., mimic, simulate, replicate, etc.) and/or be in sync with the entity's respiration in real-time (e.g., live, concurrently, and/or simultaneously with the entity's respiration).

Figure 3:
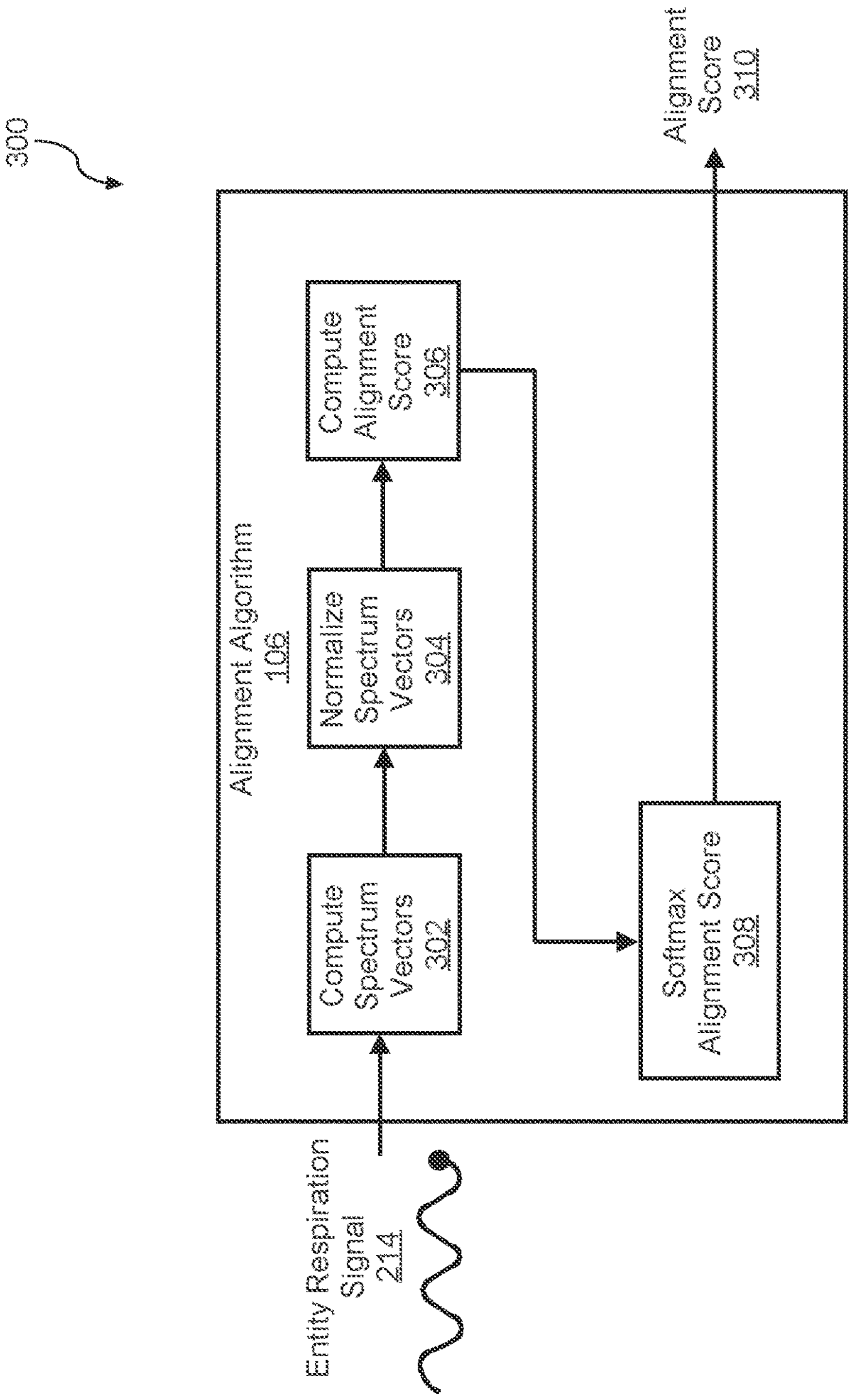

Alignment algorithm 106 can include, constitute, and/or apply a spectral similarity process to: compare the entity respiration signal and/or entity respiration amplitude signal to a suggested respiration signal; and/or determine the degree to which the entity respiration signal and/or entity respiration amplitude signal is aligned with the suggested respiration signal. The degree to which the entity respiration signal and/or entity respiration amplitude signal is aligned with the suggested respiration signal can be expressed as an alignment score that can range from, for instance, a value of approximately zero (0) to a value of approximately one (1). For example, a value of zero (0) can be indicative of a relatively poor alignment (e.g., no alignment) and/or a value of one (1) can be indicative of a relatively good alignment (e.g., complete alignment). In this manner, alignment algorithm 106 can determine an alignment score that can be indicative of the degree of the alignment of the entity respiration signal and/or entity respiration amplitude signal with the suggested respiration signal. Provided below with reference to the example embodiment depicted in FIG. 3 are details describing how alignment algorithm 106 can: compare the entity respiration signal and/or entity respiration amplitude signal to a suggested respiration signal; and/or determine the alignment score described above.

The above-described suggested respiration signal can be indicative of a suggested respiration. In one embodiment, the suggested respiration signal can be indicative of a suggested breathing pattern that can be defined and/or recommended by, for example, user computing device 710 and/or server component system 740. In this or another embodiment, the suggested respiration and/or the suggested respiration signal can be defined, generated, and/or recommended based at least in part on, for instance, one or more attributes and/or biometrics that can correspond to the entity (e.g., the entity's age, weight, height, real-time heart rate and/or average heart rate, real-time blood pressure and/or average blood pressure, etc.).

Alignment feedback data 108 can include and/or constitute the above-described alignment score and/or one or more other types of alignment feedback data that can be indicative of alignment of the entity respiration signal and/or the entity respiration amplitude signal with the suggested respiration signal. In an embodiment where user computing device 710 and/or server component system 740 implements data flow process 100, user computing device 710 and/or server component system 740 described below can generate such one or more other types of alignment feedback data based at least in part on (e.g., using) the alignment score. For instance, user computing device 710 and/or server component system 740 can generate such one or more other types of alignment feedback data such that the one or more other types of alignment feedback data are correlated with and/or correspond to the alignment score.

Alignment feedback data 108 can include and/or constitute: audio data (e.g., a digital voice, a buzzer, an audible alarm, etc.); text, numeric, and/or alphanumeric data (e.g., letters, numbers, words, a written message, a push notification, etc.); graphical data (e.g., a symbol, a character, an icon, an emoji, etc.); haptic data (e.g., vibration of a device associated with the entity such as, for instance, a smart phone, a wearable computing device, etc.); visual data (e.g., a light having intensity that is correlated with and/or varies in response to the degree of alignment), and/or another form of data. In one or more embodiments, alignment feedback data 108 can include and/or constitute an alignment visualization that can include the entity respiration signal (e.g., the entity respiration amplitude signal) and/or the suggested respiration signal. For example, such an alignment visualization can include and/or constitute a visualization of the entity respiration signal (e.g., the entity respiration amplitude signal) overlayed on and/or proximate to the suggested respiration signal (e.g., superimposed on and/or adjacent the suggested respiration signal). In one embodiment, such an alignment visualization can include and/or constitute an image (e.g., a static image) of the entity respiration signal (e.g., the entity respiration amplitude signal) overlayed on and/or proximate to the suggested respiration signal (e.g., superimposed on and/or adjacent the suggested respiration signal). In another embodiment, such an alignment visualization can include and/or constitute a video (e.g., a live, real-time video) of the entity respiration signal (e.g., the entity respiration amplitude signal) overlayed on and/or proximate to the suggested respiration signal (e.g., superimposed on and/or adjacent the suggested respiration signal).

In an embodiment where user computing device 710 and/or server component system 740 implements data flow process 100, user computing device 710 and/or server component system 740 described below can provide alignment feedback data 108 to the entity in real-time based at least in part on (e.g., in response) to the entity's respiration (e.g., live, concurrently, and/or simultaneously with the entity's respiration). For example, based at least in part on (e.g., in response to) receiving input data 102 (e.g., the continuous chirp radar signal), user computing device 710 and/or server component system 740 can (e.g., immediately upon receipt of input data 102, in real-time): implement tracking algorithm 104 to convert the respiration data into the entity respiration signal (e.g., the entity respiration amplitude signal); implement alignment algorithm 106 to compare the entity respiration signal (e.g., the entity respiration amplitude signal) to the suggested respiration signal and/or determine the alignment score corresponding to such signals; and/or provide alignment feedback data 108 (e.g., the alignment score, the above-described alignment visualization, etc.) to the entity in real-time in response to the entity's respiration (e.g., live, concurrently, and/or simultaneously with the entity's respiration). In at least one embodiment, user computing device 710 and/or server component system 740 can perform such operations in real-time while the entity is performing, for instance, a guided breathing exercise that can be defined and/or communicated to the entity by user computing device 710 and/or server component system 740 based on the above-described suggested respiration and/or suggested respiration signal that can be defined and/or generated by user computing device 710 and/or server component system 740 as described above. For instance, user computing device 710 and/or server component system 740 can perform such operations in real-time while the entity is attempting to align the entity's respiration with the suggested respiration and/or align the entity respiration signal (e.g., the entity respiration amplitude signal) with the suggested respiration signal.

FIG. 2 illustrates a data flow diagram of an example, non-limiting data flow process 200 according to one or more example embodiments of the present disclosure. A computing system described herein can implement data flow process 200 to facilitate a closed-loop, contactless respiration guidance process that provides quantified alignment feedback data in real-time in accordance with example embodiments of the present disclosure. For example, user computing device 710 and/or server component system 740 described below and illustrated in FIG. 7 can implement (e.g., execute, run, etc.) tracking algorithm 104 to perform data flow process 200 to facilitate a closed-loop, contactless respiration guidance process that provides quantified alignment feedback data in real-time in accordance with example embodiments of the present disclosure.

Data flow process 200 can include and/or constitute a data flow process of data flowing through tracking algorithm 104. For example, data flow process 200 can include and/or constitute a data flow process of input data 102 and/or the above-described respiration data through tracking algorithm 104. More specifically, in the example embodiment depicted in FIG. 2, data flow process 200 can include and/or constitute a data flow process of input data 102 and/or the respiration data through tracking algorithm 104 to convert the respiration data into an entity respiration signal 214 such that entity respiration signal 214 can track (e.g., mimic, simulate, replicate, etc.) and/or be in sync with the entity's respiration in real-time (e.g., live, concurrently, and/or simultaneously with the entity's respiration). In at least one embodiment described herein, entity respiration signal 214 can include and/or constitute an entity respiration amplitude signal.

As illustrated in the example embodiment depicted in FIG. 2, at 202, tracking algorithm 104 can remove clutter from input data 102. For example, tracking algorithm 104 can remove noise data from input data 102 and/or the respiration data using an exponential filter and/or an exponential smoothing process. The noise data can include and/or constitute data that can be indicative of at least one movement corresponding to one or more second entities (e.g., movements of objects and/or other people).

At 204, tracking algorithm 104 can map out a range that can be associated with input data 102 and/or the respiration data using an exponential filter and/or an exponential smoothing process. The range can include and/or constitute at least a portion of the entity's respiration data.

At 206, tracking algorithm 104 can normalize the range into a range probability map that can include and/or constitute multiple range bins. Each of the multiple range bins can include and/or constitute at least a portion of the respiration data.

At 208, tracking algorithm 104 can apply one or more inertia functions to the range probability map and/or the multiple range bins to determine a center-of-mass that can correspond to the range probability map and/or the multiple range bins.

At 210, tracking algorithm 104 can extract phase data (e.g., from the probability map) that can correspond to the center-of-mass. The phase data can be indicative of a phase signal (e.g., a wrapped phase signal or an unwrapped phase signal) that can correspond to the center-of-mass.

At 212, tracking algorithm 104 can apply a filter to the phase signal to obtain and output entity respiration signal 214 (e.g., an entity respiration amplitude signal). The filter can be operable to remove data that can be indicative of defined entity movements that can be associated with the entity's respiration (e.g., subtle movements the entity makes while inhaling and/or exhaling).

In embodiments where input data 102 includes and/or constitutes a combination of different types of input data that each have a different type of respiration data as described above, tracking algorithm 104 can perform the above-described operations with respect to each different type of input data to convert all the different types of respiration data into entity respiration signal 214. For example, in embodiments where input data 102 includes and/or constitutes a combination of, for instance, radar data indicative of the entity's respiration, sonar data indicative of the entity's respiration, and video data indicative of the entity's respiration, tracking algorithm 104 can perform the above-described operations with respect to each different type of input data to convert all the different types of respiration data into entity respiration signal 214. For instance, in these embodiments, tracking algorithm 104 can convert all the different types of respiration data into a single entity respiration signal 214 such that entity respiration signal 214 can include, constitute, and/or account for all such different types of respiration data.

FIG. 3 illustrates a data flow diagram of an example, non-limiting data flow process 300 according to one or more example embodiments of the present disclosure. A computing system described herein can implement data flow process 300 to facilitate a closed-loop, contactless respiration guidance process that provides quantified alignment feedback data in real-time in accordance with example embodiments of the present disclosure. For example, user computing device 710 and/or server component system 740 described below and illustrated in FIG. 7 can implement (e.g., execute, run, etc.) alignment algorithm 106 to perform data flow process 300 to facilitate a closed-loop, contactless respiration guidance process that provides quantified alignment feedback data in real-time in accordance with example embodiments of the present disclosure.

Data flow process 300 can include and/or constitute a data flow process of data flowing through alignment algorithm 106. For example, data flow process 300 can include and/or constitute a data flow process of entity respiration signal 214 (e.g., an entity respiration amplitude signal) through alignment algorithm 106. More specifically, in the example embodiment depicted in FIG. 3, data flow process 300 can include and/or constitute a data flow process of entity respiration signal 214 through alignment algorithm 106 to compare entity respiration signal 214 to a suggested respiration signal and/or determine the degree to which entity respiration signal 214 is aligned with the suggested respiration signal. That is, for instance, data flow process 300 can include and/or constitute a data flow process of entity respiration signal 214 through alignment algorithm 106 to determine alignment score 310.

As illustrated in the example embodiment depicted in FIG. 3, at 302, alignment algorithm 106 can compute spectrum vectors of respiration data for phase invariance by: computing a first spectrum vector that can correspond to the entity's respiration data and/or entity respiration signal 214 (e.g., an entity respiration amplitude signal); and computing a second spectrum vector that can correspond to suggested respiration data (e.g., data indicative of a suggested respiration) and/or a corresponding suggested respiration signal. In at least one embodiment, the suggested respiration data and/or the suggested respiration signal corresponding thereto can be defined, generated, and/or recommended by, for instance, user computing device 710 and/or server component system 740 as described above.

At 304, alignment algorithm 106 can apply a normalization function to the first spectrum vector and the second spectrum vector to compute a first normalized spectrum vector and a second normalized spectrum vector, respectively. For example, alignment algorithm 106 can apply an L2-normalization function to the first spectrum vector and the second spectrum vector to compute a first L2-normalized spectrum vector and a second L2-normalized spectrum vector, respectively.

At 306, alignment algorithm 106 can compute an alignment score of the first and second L2-normalized spectrum vectors. For example, alignment algorithm 106 can perform a dot product operation to compute an alignment score of the first and second L2-normalized spectrum vectors.

At 308, alignment algorithm 106 can apply a softmax function to the alignment score to obtain and output alignment score 310. Alignment algorithm 106 can apply the softmax function to improve dynamic range associated with alignment score 310.

FIG. 4 illustrates a data flow diagram of an example, non-limiting data flow process 400 according to one or more example embodiments of the present disclosure. A computing system described herein can implement data flow process 400 to facilitate a closed-loop, contactless respiration guidance process that provides quantified alignment feedback data in real-time in accordance with example embodiments of the present disclosure. For example, user computing device 710 and/or server component system 740 described below and illustrated in FIG. 7 can implement (e.g., execute, run, etc.) tracking algorithm 104 to perform data flow process 400 to facilitate a closed-loop, contactless respiration guidance process that provides quantified alignment feedback data in real-time in accordance with example embodiments of the present disclosure.

Data flow process 400 can include and/or constitute a data flow process of data flowing through tracking algorithm 104. Data flow process 400 can include and/or constitute an example, non-limiting alternative embodiment of data flow process 200 described above and illustrated in FIG. 2. For example, data flow process 400 can include and/or constitute a data flow process of a continuous chirp radar signal 402 through tracking algorithm 104 instead of input data 102. More specifically, in the example embodiment depicted in FIG. 4, data flow process 400 can include and/or constitute a data flow process of continuous chirp radar signal 402 through tracking algorithm 104 to convert continuous chirp radar signal 402 into an entity respiration amplitude signal 418 such that entity respiration amplitude signal 418 can track (e.g., mimic, simulate, replicate, etc.) and/or be in sync with the entity's respiration in real-time (e.g., live, concurrently, and/or simultaneously with the entity's respiration).

As illustrated in the example embodiment depicted in FIG. 4, at 404, tracking algorithm 104 can remove clutter from continuous chirp radar signal 402. For example, tracking algorithm 104 can remove noise data from continuous chirp radar signal 402 using an exponential filter and/or an exponential smoothing process. The noise data can include and/or constitute data that can be indicative of at least one movement corresponding to one or more second entities (e.g., movements of objects and/or other people).

At 406, tracking algorithm 104 can map out a range that can be associated with continuous chirp radar signal 402 using an exponential filter and/or an exponential smoothing process. The range can include and/or constitute at least a portion of the entity's respiration data.

At 408, tracking algorithm 104 can normalize the range into a range probability map that can include and/or constitute multiple range bins. Each of the multiple range bins can include and/or constitute at least a portion of the respiration data.

At 410, tracking algorithm 104 can apply one or more inertia functions to the range probability map and/or the multiple range bins to determine a center-of-mass that can correspond to the range probability map and/or the multiple range bins.

At 412, tracking algorithm 104 can extract phase data (e.g., from the probability map) that can correspond to the center-of-mass. The phase data can be indicative of a wrapped phase signal that can correspond to the center-of-mass.

At 414, tracking algorithm 104 can perform a signal phase unwrapping process on the phase data and/or the wrapped phase signal to obtain a continuous phase signal that can correspond to the center-of-mass.

At 416, tracking algorithm 104 can apply a filter to the continuous phase signal to obtain and output entity respiration amplitude signal 418. The filter can be operable to remove data that can be indicative of defined entity movements that can be associated with the entity's respiration (e.g., subtle movements the entity makes while inhaling and/or exhaling).

In an additional and/or alternative embodiment, entity respiration amplitude signal 418 can be input into alignment algorithm 106 to compare entity respiration amplitude signal 418 to a suggested respiration signal and/or determine the degree to which entity respiration amplitude signal 418 is aligned with the suggested respiration signal. That is, for instance, entity respiration amplitude signal 418 can be input into alignment algorithm 106 (e.g., by user computing device 710 and/or server component system 740) to determine alignment score 310 as described above with reference to FIG. 3.

Figure 5A:
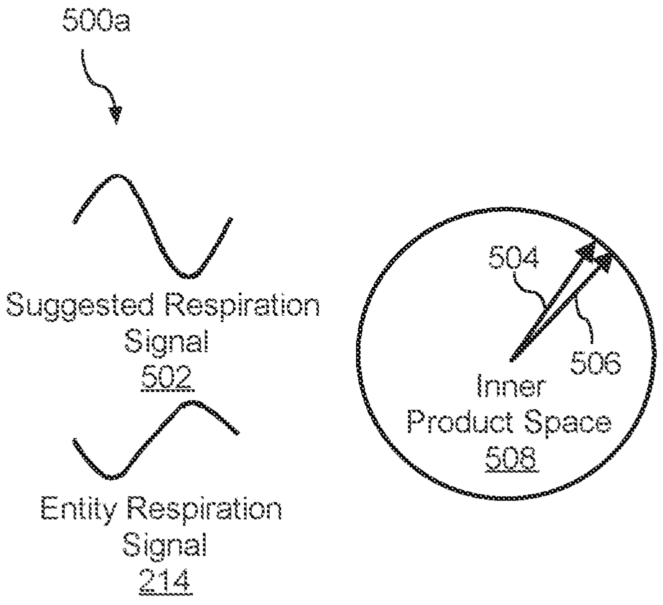
FIGS. 5A and 5B each illustrate a diagram of an example, non-limiting signal assessment process according to one or more example embodiments of the present disclosure.
Figure 5B:
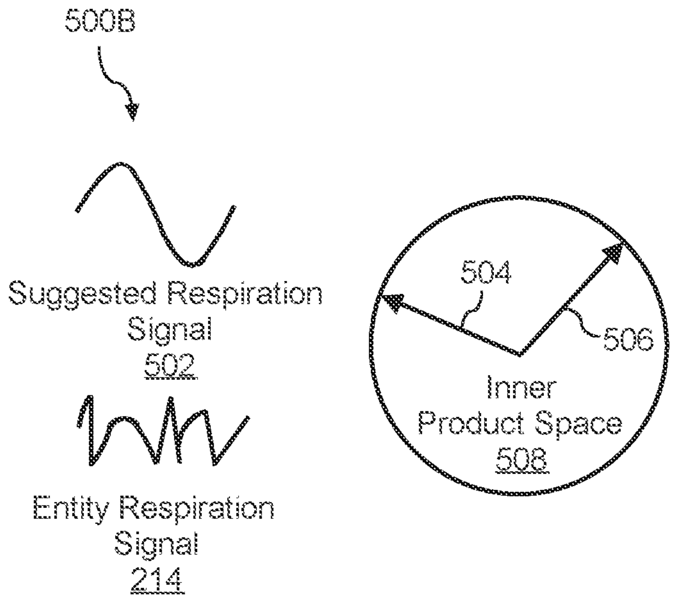

FIGS. 5A and 5B each illustrate a diagram of an example, non-limiting signal assessment process 500*a* and 500*b*, respectively, according to one or more example embodiments of the present disclosure. A computing system described herein can implement signal assessment process 500*a* and/or 500*b* to facilitate a closed-loop, contactless respiration guidance process that provides quantified alignment feedback data in real-time in accordance with example embodiments of the present disclosure. For example, user computing device 710 and/or server component system 740 described below and illustrated in FIG. 7 can implement (e.g., execute, run, etc.) tracking algorithm 104 and/or alignment algorithm 106 to perform signal assessment process 500*a* and/or 500*b* to facilitate a closed-loop, contactless respiration guidance process that provides quantified alignment feedback data in real-time in accordance with example embodiments of the present disclosure.

As described above with reference to FIGS. 1, 2, 3, and 4, user computing device 710 and/or server component system 740 can implement (e.g., execute, run, etc.) tracking algorithm 104 to generate entity respiration signal 214. In this example, user computing device 710 and/or server component system 740 can generate a suggested respiration signal 502 corresponding to a suggested respiration (e.g., data indicative of a suggested respiration) that can be defined and/or recommended by user computing device 710 and/or server component system 740 as described above. In this example, user computing device 710 and/or server component system 740 can implement (e.g., execute, run, etc.) alignment algorithm 106 to compute: a spectrum vector 504 that can correspond to the entity's respiration data and/or entity respiration signal 214 (e.g., an entity respiration amplitude signal); and a spectrum vector 506 that can correspond to the suggested respiration (e.g., data indicative of a suggested respiration) and/or suggested respiration signal 502. In this example, user computing device 710 and/or server component system 740 can implement (e.g., execute, run, etc.) alignment algorithm 106 to compute spectrum vector 504 and spectrum vector 506 in an inner product space 508 as illustrated in FIGS. 5A and 5B.

In the example embodiments depicted in FIGS. 5A and 5B, inner product space 508 can include and/or constitute an L2-normalized vector space. In these embodiments, spectrum vector 504 and spectrum vector 506 can each describe and/or correspond to a normalized vector (e.g., an L2-normalized vector). In embodiments where spectrum vector 504 and spectrum vector 506 are close to each another (e.g., as illustrated by the depiction of spectrum vector 504 and spectrum vector 506 in inner product space 508 shown in FIG. 5A), that means the dot product will be maximized. In embodiments where spectrum vector 504 and spectrum vector 506 are not close to each other, for instance, they are separated apart from each other (e.g., as illustrated by the depiction of spectrum vector 504 and spectrum vector 506 in inner product space 508 shown in FIG. 5B), that means the dot product will be small. In the above embodiments, this is because mathematically, the dot product of L2-normalized vectors is used to measure the "angle" between the L2-normalized vectors in the inner product space. For instance, in the example embodiments depicted in FIGS. 5A and 5B, user computing device 710 and/or server component system 740 can implement alignment algorithm 106 to take the dot product of spectrum vector 504 and spectrum vector 506 as described herein to determine the angle between spectrum vector 504 and spectrum vector 506 in inner product space 508. In these or other example embodiments, user computing device 710 and/or server component system 740 can thereby determine the degree to which the entity's respiration (e.g., represented by entity respiration signal 214 in FIGS. 5A and 5B) is aligned with the suggested respiration (e.g., represented by suggested respiration signal 502 in FIGS. 5A and 5B).

In one embodiment, based on implementing signal assessment process 500*a*, user computing device 710 and/or server component system 740 can determine that entity respiration signal 214 has a relatively good alignment with suggested respiration signal 502. As such, user computing device 710 and/or server component system 740 can further compute and/or output (e.g., via alignment algorithm 106) an alignment score (e.g., alignment score 310) having a value reflecting such a relatively good alignment of entity respiration signal 214 with suggested respiration signal 502 (e.g., a value of approximately one (1)).

In another embodiment, based on implementing signal assessment process 500*b*, user computing device 710 and/or server component system 740 can determine that entity respiration signal 214 has a relatively poor alignment with suggested respiration signal 502. As such, user computing device 710 and/or server component system 740 can further compute and/or output (e.g., via alignment algorithm 106) an alignment score (e.g., alignment score 310) having a value reflecting such a relatively poor alignment of entity respiration signal 214 with suggested respiration signal 502 (e.g., a value of approximately zero (0)).

Figure 6:
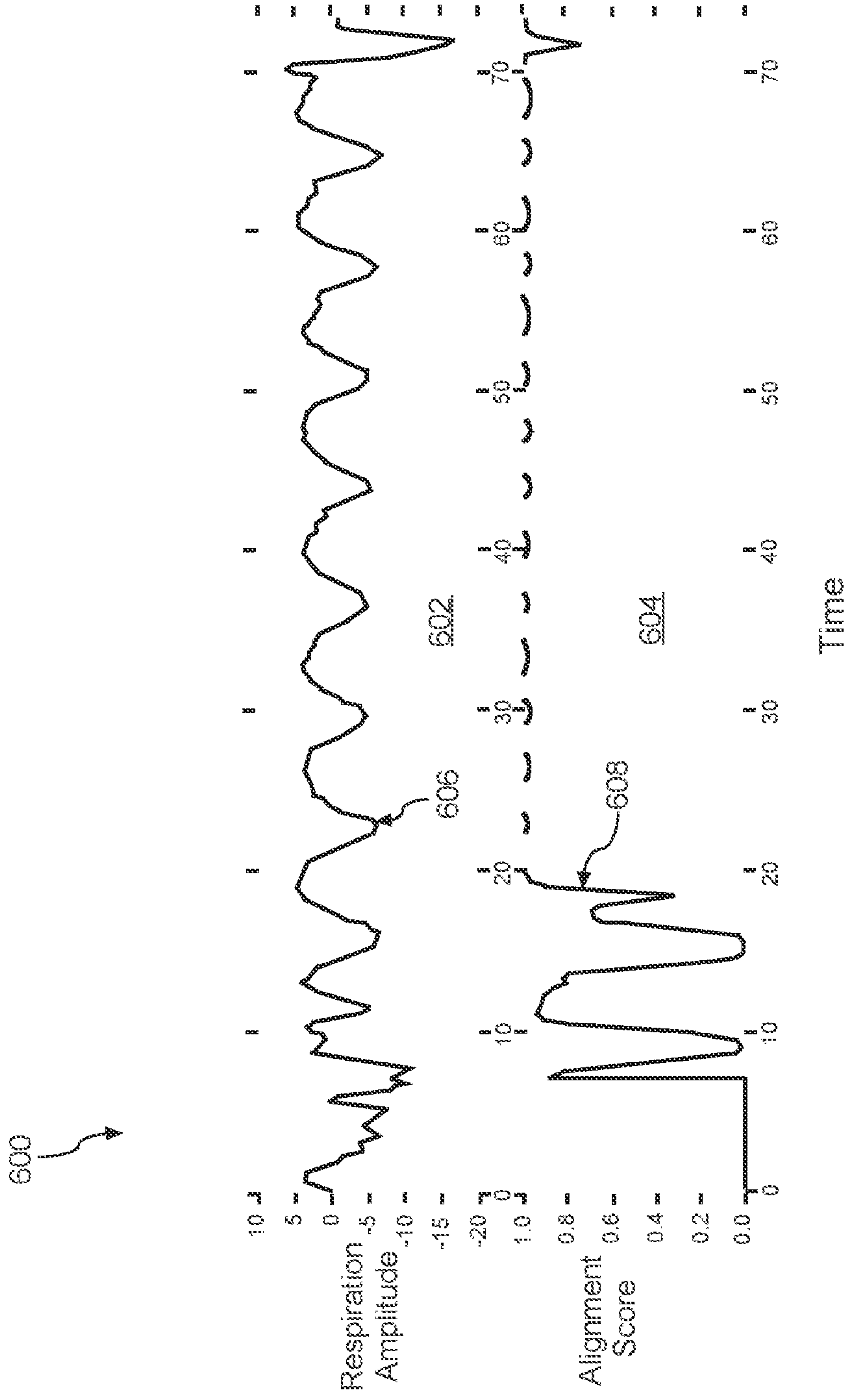
FIG. 6 illustrates a diagram of example, non-limiting alignment feedback data according to one or more example embodiments of the present disclosure.

FIG. 6 illustrates a diagram of example, non-limiting alignment feedback data 600 according to one or more example embodiments of the present disclosure. Alignment feedback data 600 can include and/or constitute an example, non-limiting embodiment of alignment feedback data 108 described above with reference to FIG. 1. For example, alignment feedback data 600 can include and/or constitute an example, non-limiting embodiment of the above-described alignment visualization that can include and/or constitute a visualization of an entity respiration signal (e.g., an entity respiration amplitude signal) and/or a suggested respiration signal. In one embodiment, alignment feedback data 600 can include and/or constitute an image (e.g., a static image) of an entity respiration signal (e.g., an entity respiration amplitude signal) and/or a suggested respiration signal. In another embodiment, alignment feedback data 600 can include and/or constitute a video (e.g., a live, real-time video) of an entity respiration signal (e.g., an entity respiration amplitude signal) and/or a suggested respiration signal.

A computing system according to example embodiments of the present disclosure can implement one or more of the processes, algorithms, and/or methods (e.g., computer-implemented methods) described herein to generate alignment feedback data 600. For example, to generate alignment feedback data 600, user computing device 710 and/or server component system 740 described below and illustrated in FIG. 7 can implement data flow process 100, tracking algorithm 104, alignment algorithm 106, data flow process 200, data flow process 300, data flow process 400, signal assessment process 500*a* and/or 500*b*, and/or computer-implemented method 800 and/or 900 described below and illustrated in FIGS. 8 and 9, respectively.

As illustrated in the example embodiment depicted in FIG. 6, alignment feedback data 600 can include an entity respiration signal plot 602 of an entity respiration curve 606 and/or an alignment score plot 604 of an alignment score curve 608. In this embodiment, entity respiration signal plot 602 charts the respiration amplitude values of entity respiration curve 606 over time and alignment score plot 604 charts the alignment score values of alignment score curve 608 over time.

In one embodiment, entity respiration curve 606 can correspond to and/or represent entity respiration signal 214. In another embodiment, entity respiration curve 606 can correspond to and/or represent entity respiration amplitude signal 418. In either of the above embodiments, alignment score curve 608 can correspond to and/or represent alignment score 310. In the example embodiment depicted in FIG. 6, entity respiration signal plot 602 and alignment score plot 604 indicate that an entity respiration signal corresponding to entity respiration curve 606 (e.g., entity respiration signal 214 or entity respiration amplitude signal 418) has a relatively good alignment with a suggested respiration signal (not illustrated).

Figure 7:
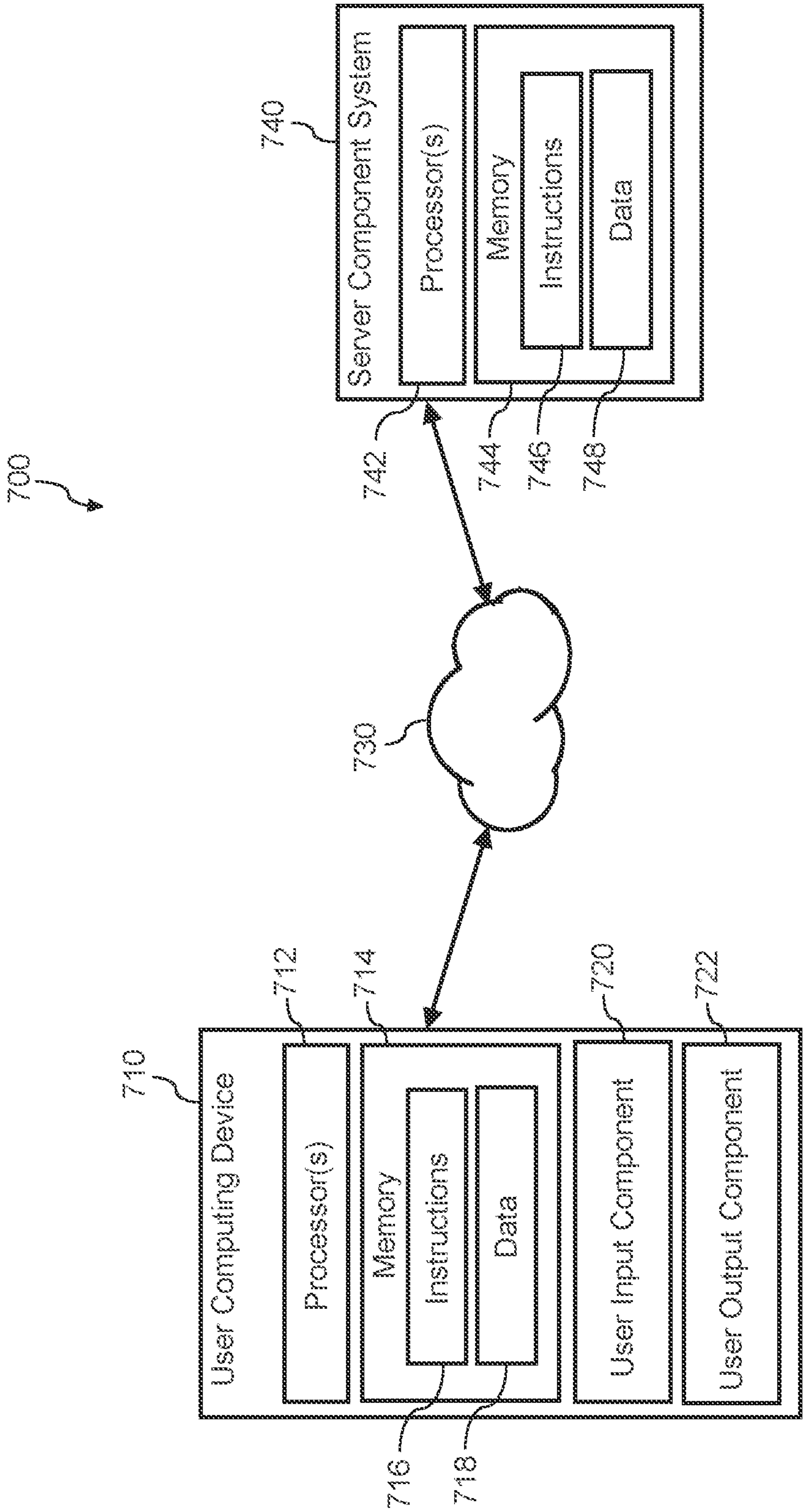
FIG. 7 illustrates a block diagram of an example, non-limiting computing system according to one or more example embodiments of the present disclosure.

FIG. 7 illustrates a block diagram of an example, non-limiting computing system 700 according to one or more example embodiments of the present disclosure. Computing system 700 can include user computing device 710 and/or server computing system 740 that can be communicatively coupled over a network 730. Computing system 700, user computing device 710, and/or server component system 740 can be used to implement one or more of the processes, algorithms, and/or methods (e.g., computer-implemented methods) described herein to facilitate a closed-loop, contactless respiration guidance process that provides quantified alignment feedback data in real-time.

The user computing device 710 can be any type of computing device, such as, for example, a personal computing device (e.g., laptop or desktop), a mobile computing device (e.g., smartphone or tablet), a gaming console or controller, a wearable computing device, an embedded computing device, or any other type of computing device.

The user computing device 710 includes one or more processors 712 and a memory 714. The one or more processors 712 can be any suitable processing device (e.g., a processor core, a microprocessor, an ASIC, an FPGA, a controller, a microcontroller, etc.) and can be one processor or a plurality of processors that are operatively connected. The memory 714 can include one or more non-transitory computer-readable storage media, such as RAM, ROM, EEPROM, EPROM, flash memory devices, magnetic disks, etc., and combinations thereof. The memory 714 can store data 716 and instructions 718 which are executed by the processor 712 to cause the user computing device 710 to perform operations, such as any of the operations described herein. In at least one embodiment, the data 716 and/or the instructions 718 can include and/or constitute, for instance, tracking algorithm 104 and/or alignment algorithm 106.

The user computing device 710 can also include one or more user input components 720 that receive, obtain, capture, and/or collect input data (e.g., user input, input data 102, the above-described respiration data, etc.). For example, the user input component 720 can be a touch-sensitive component (e.g., a touch-sensitive display screen or a touch pad) that is sensitive to the touch of a user input object (e.g., a finger or a stylus). The touch-sensitive component can serve to implement a virtual keyboard. Other example user input components include a microphone, a traditional keyboard, or other means by which a user can provide user input. In at least one embodiment, the user input component 720 can include and/or constitute the above-described contactless sources and/or devices that can capture, collect, and/or otherwise obtain input data (e.g., input data 102) and/or respiration data of an entity without physically engaging the entity (e.g., without touching the entity). For instance, the user input component 720 can include and/or constitute a radar device (e.g., a high frequency radar, a real-time motion tracking radar, an FMCW radar, etc.), a sonar device, a camera device, an audio device (e.g., a microphone, etc.), and/or another contactless source and/or device that can capture, collect, and/or otherwise obtain such input data and/or respiration data without physically engaging the entity. The user computing device 710 can also include a user output component 722. The user output component 722 can provide information and can include, for instance, a display screen, audio output device, haptic device, or other suitable device.

The server computing system 740 includes one or more processors 742 and a memory 744. The one or more processors 742 can be any suitable processing device (e.g., a processor core, a microprocessor, an ASIC, an FPGA, a controller, a microcontroller, etc.) and can be one processor or a plurality of processors that are operatively connected. The memory 744 can include one or more non-transitory computer-readable storage media, such as RAM, ROM, EEPROM, EPROM, flash memory devices, magnetic disks, etc., and combinations thereof. The memory 744 can store data 746 and instructions 748 which are executed by the processor 742 to cause the server computing system 740 to perform operations, such as any of the operations described herein.

In some implementations, the server computing system 740 includes or is otherwise implemented by one or more server computing devices. In instances in which the server computing system 740 includes plural server computing devices, such server computing devices can operate according to sequential computing architectures, parallel computing architectures, or some combination thereof.

The network 730 can be any type of communications network, such as a local area network (e.g., intranet), wide area network (e.g., Internet), or some combination thereof and can include any number of wired or wireless links. In general, communication over the network 7300 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

Figure 8:
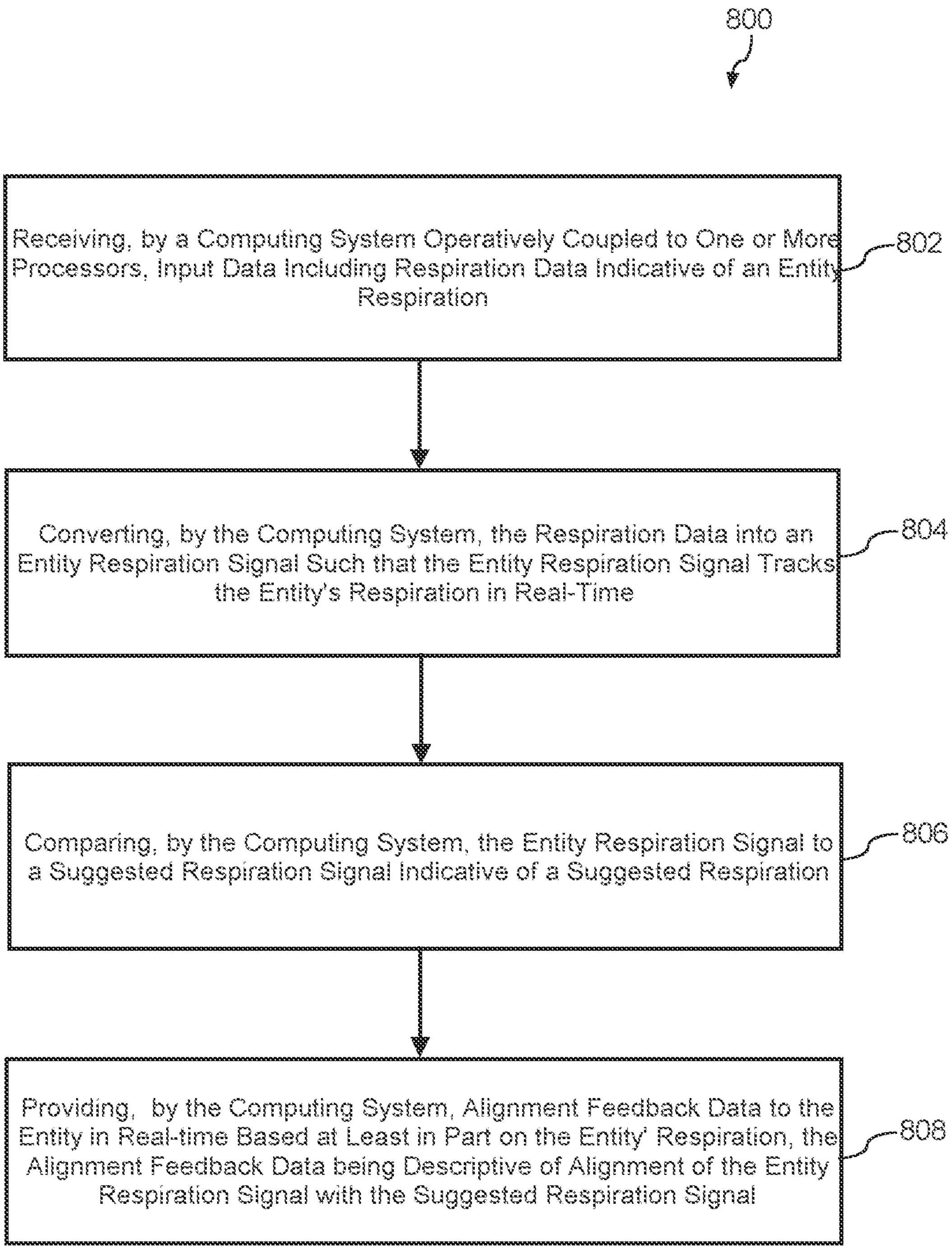
FIGS. 8 and 9 each illustrate a flow diagram of an example, non-limiting computer-implemented method according to one or more example embodiments of the present disclosure.

FIG. 8 illustrates a flow diagram of an example, non-limiting computer-implemented method 800 according to one or more example embodiments of the present disclosure. Computer-implemented method 800 may be implemented using, for instance, computing system 700, user computing device 710, and/or server component system 740 described above with reference to FIG. 7. The example embodiment illustrated in FIG. 8 depicts operations performed in a particular order for purposes of illustration and discussion. Those of ordinary skill in the art, using the disclosures provided herein, will understand that various operations or steps of computer-implemented method 800 or any of the other methods disclosed herein may be adapted, modified, rearranged, performed simultaneously, include operations not illustrated, and/or modified in various ways without deviating from the scope of the present disclosure.

At 802, computer-implemented method 800 can include receiving, by a computing system (e.g., computing system 700, user computing device 710, and/or server component system 740) operatively coupled to one or more processors (e.g., one or more processors 712), input data (e.g., input data 102, continuous chirp radar signal 402, etc.) including respiration data indicative of an entity's respiration.

At 804, computer-implemented method 800 can include converting, by the computing system (e.g., via tracking algorithm 104, data flow process 200, data flow process 400, etc.), the respiration data into an entity respiration signal (e.g., entity respiration signal 214, entity respiration amplitude signal 418, etc.) such that the entity respiration signal tracks (e.g., mimics, simulates, replicates, etc.) the entity's respiration in real-time (e.g., live, concurrently, and/or simultaneously with the entity's respiration).

At 806, computer-implemented method 800 can include comparing, by the computing system (e.g., via alignment algorithm 106, data flow process 300, signal assessment process 500*a* and/or 500*b*, etc.), the entity respiration signal to a suggested respiration signal indicative of a suggested respiration (e.g., suggested respiration signal 502 or another suggested respiration signal that can be generated by user computing device 710 and/or server component system 740 as described above with reference to FIGS. 1, 2, 3, 4, 5A, and 5B).

At 808, computer-implemented method 800 can include providing, by the computing system (e.g., via user output component 722, network 730, a WPAN, etc.), alignment feedback data (e.g., alignment feedback data 108, alignment score 310, alignment feedback data 600, alignment feedback data 1000*a* and/or 1000*b* described below with reference to FIGS. 10A and 10B, respectively) to the entity in real-time based at least in part on the entity's respiration (e.g., live, concurrently, and/or simultaneously with the entity's respiration), the alignment feedback data being indicative of alignment of the entity respiration signal with the suggested respiration signal.

Figure 9:
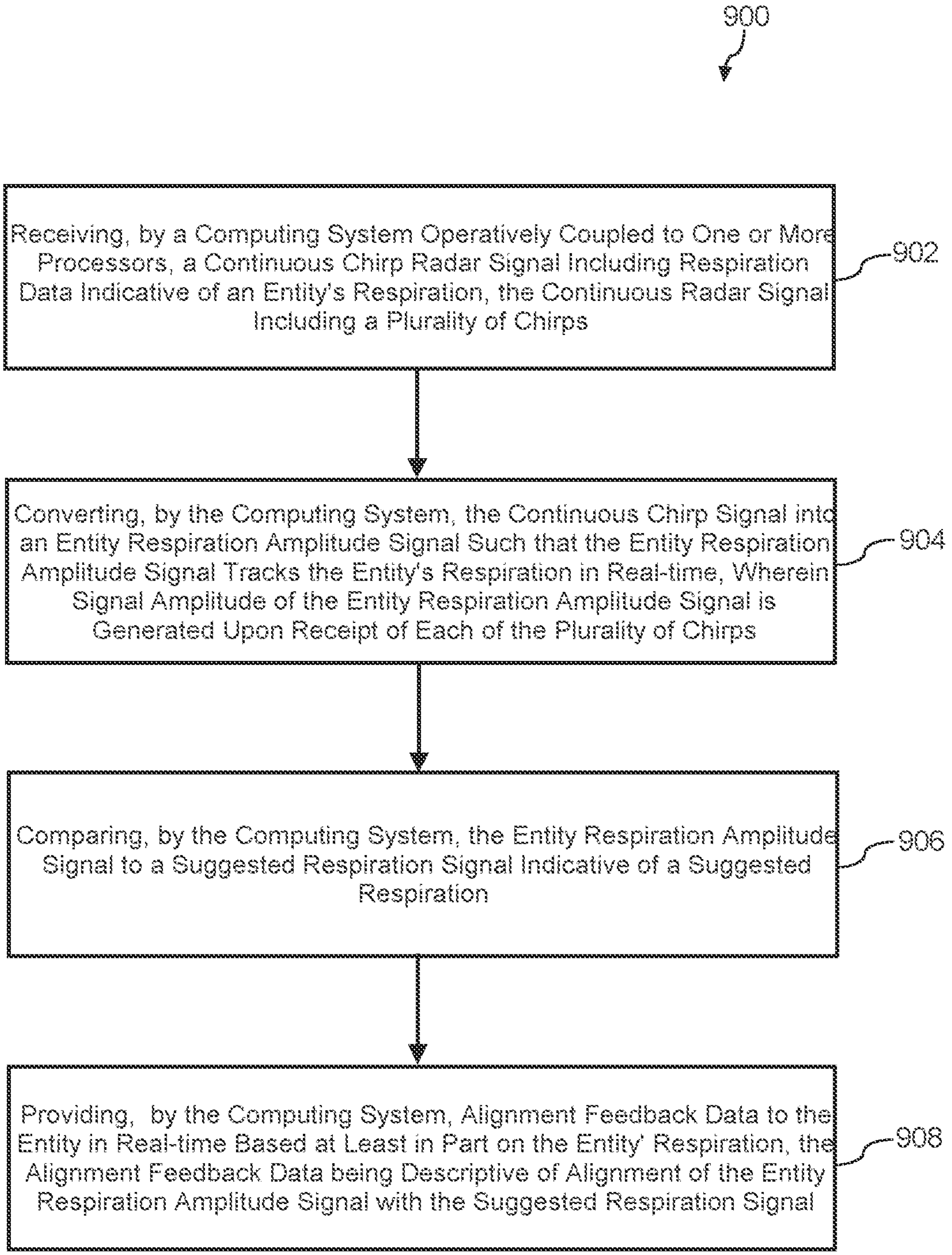

FIG. 9 illustrates a flow diagram of an example, non-limiting computer-implemented method 900 according to one or more example embodiments of the present disclosure. Computer-implemented method 900 may be implemented using, for instance, computing system 700, user computing device 710, and/or server component system 740 described above with reference to FIG. 7. The example embodiment illustrated in FIG. 9 depicts operations performed in a particular order for purposes of illustration and discussion. Those of ordinary skill in the art, using the disclosures provided herein, will understand that various operations or steps of computer-implemented method 900 or any of the other methods disclosed herein may be adapted, modified, rearranged, performed simultaneously, include operations not illustrated, and/or modified in various ways without deviating from the scope of the present disclosure.

At 902, computer-implemented method 900 can include receiving, by a computing system (e.g., user computing device 710 and/or server component system 740) operatively coupled to one or more processors (e.g., one or more processors 712), a continuous chirp radar signal (e.g., continuous chirp radar signal 402) including respiration data indicative of an entity's respiration, the continuous chirp radar signal including a plurality of chirps.

At 904, computer-implemented method 900 can include converting, by the computing system (e.g., via tracking algorithm 104, data flow process 400, etc.), the continuous chirp radar signal into an entity respiration amplitude signal (e.g., entity respiration amplitude signal 418, etc.) such that the entity respiration amplitude signal tracks (e.g., mimics, simulates, replicates, etc.) the entity's respiration in real-time (e.g., live, concurrently, and/or simultaneously with the entity's respiration), where signal amplitude of the entity respiration amplitude signal is generated upon receipt of each of the plurality of chirps.

At 906, computer-implemented method 900 can include comparing, by the computing system (e.g., via alignment algorithm 106, data flow process 300, signal assessment process 500*a* and/or 500*b*, etc.), the entity respiration amplitude signal to a suggested respiration signal indicative of a suggested respiration (e.g., suggested respiration signal 502 or another suggested respiration signal that can be generated by user computing device 710 and/or server component system 740 as described above with reference to FIGS. 1, 2, 3, 4, 5A, and 5B).

At 908, computer-implemented method 900 can include providing, by the computing system (e.g., via user output component 722, network 730, a WPAN, etc.), alignment feedback data (e.g., alignment feedback data 108, alignment score 310, alignment feedback data 600, and/or alignment feedback data 1000*a* and/or 1000*b* described below with reference to FIGS. 10A and 10B, respectively) to the entity in real-time based at least in part on the entity's respiration (e.g., live, concurrently, and/or simultaneously with the entity's respiration), the alignment feedback data being indicative of alignment of the entity respiration amplitude signal with the suggested respiration signal.

Figure 10A:
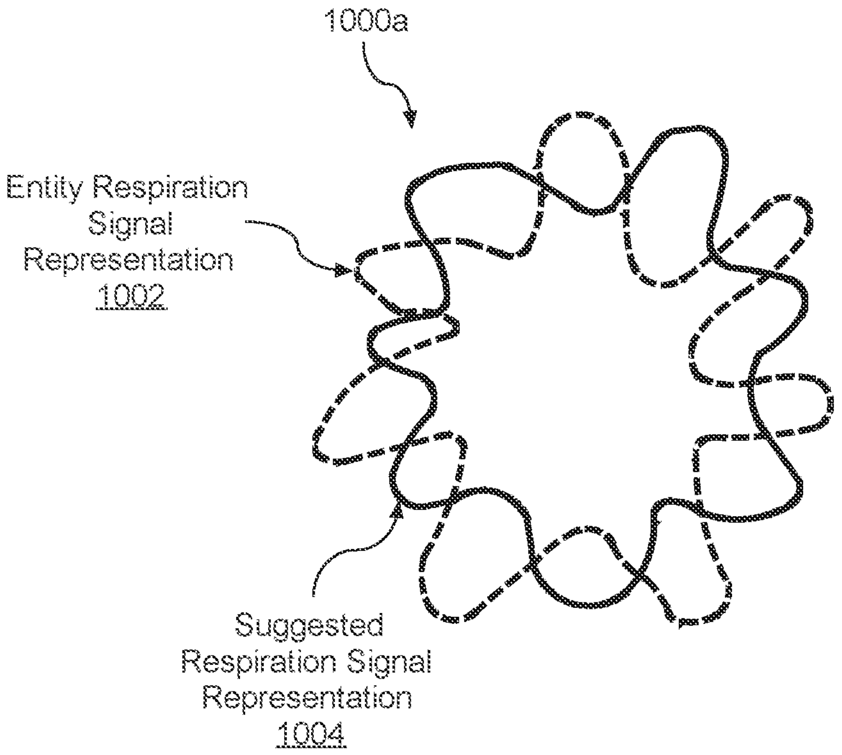
FIGS. 10A and 10B each illustrate a diagram of example, non-limiting alignment feedback data according to one or more example embodiments of the present disclosure.
Figure 10B:
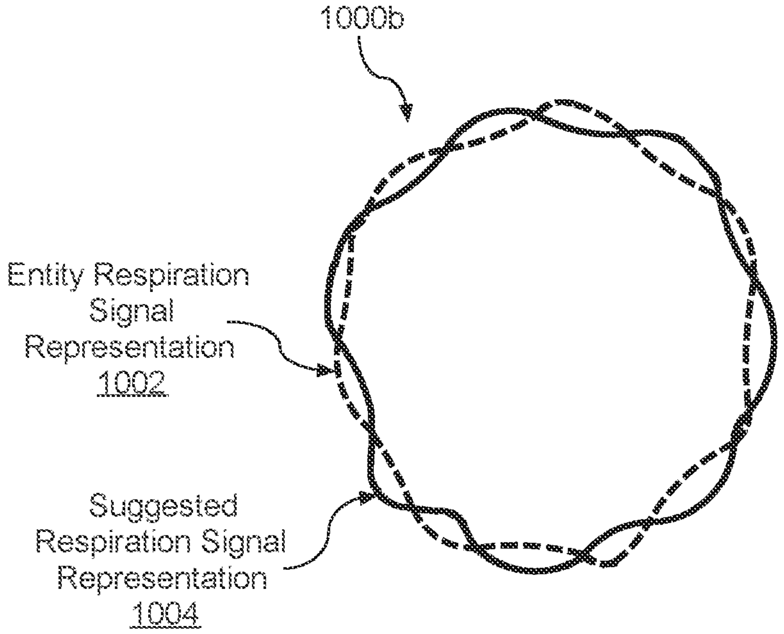

FIGS. 10A and 10B each illustrate a diagram of an example, non-limiting alignment feedback data 1000*a* and 1000*b*, respectively according to one or more example embodiments of the present disclosure. Alignment feedback data 1000*a* and/or 1000*b* can include and/or constitute an example, non-limiting embodiment of alignment feedback data 108 described above with reference to FIG. 1. Additionally, or alternatively, alignment feedback data 1000*a* and/or 1000*b* can include and/or constitute an example, non-limiting alternative embodiment of alignment feedback data 600 described above with reference to FIG. 6. For example, alignment feedback data 1000*a* and/or 1000*b* can include and/or constitute an example, non-limiting embodiment of the above-described alignment visualization that can include and/or constitute a visualization of an entity respiration signal (e.g., an entity respiration amplitude signal) overlayed on and/or proximate to a suggested respiration signal (e.g., superimposed on and/or proximate to a suggested respiration signal). In one embodiment, alignment feedback data 1000*a* and/or 1000*b* can include and/or constitute an image (e.g., a static image) of an entity respiration signal (e.g., an entity respiration amplitude signal) overlayed on and/or proximate to a suggested respiration signal (e.g., superimposed on and/or adjacent to a suggested respiration signal). In another embodiment, alignment feedback data 1000*a* and/or 1000*b* can include and/or constitute a video (e.g., a live, real-time video) of an entity respiration signal (e.g., an entity respiration amplitude signal) overlayed on and/or proximate to a suggested respiration signal (e.g., superimposed on and/or adjacent to a suggested respiration signal).

A computing system according to example embodiments of the present disclosure can implement one or more of the processes, algorithms, and/or methods (e.g., computer-implemented methods) described herein to generate alignment feedback data 1000*a* and/or 1000*b*. For example, to generate alignment feedback data 1000*a* and/or 1000*b*, user computing device 710 and/or server component system 740 can implement data flow process 100, tracking algorithm 104, alignment algorithm 106, data flow process 200, data flow process 300, data flow process 400, signal assessment process 500*a* and/or 500*b*, and/or computer-implemented method 800 and/or 900. In one example embodiment, user computing device 710 and/or server component system 740 can implement data flow process 100, tracking algorithm 104, and/or alignment algorithm 106 to: perform the above-described comparison of an entity respiration signal (e.g., entity respiration signal 214 or entity respiration amplitude signal 418) to a suggested respiration signal (e.g., suggested respiration signal 502); and/or to determine the degree to which such an entity respiration signal is aligned (or not) with such a suggested respiration signal as described above with reference to FIGS. 1-4. In this embodiment, user computing device 710 and/or server component system 740 can generate alignment feedback data 1000*a* and/or 1000*b* based at least in part on such comparison and determination of the degree of alignment of such an entity respiration signal with such a suggested respiration signal. It should be appreciated that user computing device 710 and/or server component system 740 can generate and/or provide alignment feedback data 1000*a* and/or 1000*b* to an entity implementing one or more embodiments described herein to provide the entity with user-friendly alignment feedback data that can allow the entity to conveniently, easily, and/or quickly interpret the data to understand how well or poorly the entity is mimicking (e.g., simulating) the suggested respiration signal.

As illustrated in the example embodiments depicted in FIGS. 10A and 10B, alignment feedback data 1000*a* and 1000*b* can each include an entity respiration signal representation 1002 and/or a suggested respiration signal representation 1004. In this embodiment, entity respiration signal representation 1002 can be overlayed on and/or proximate to suggested respiration signal representation 1004 (e.g., superimposed on and/or proximate to suggested respiration signal representation 1004).

Entity respiration signal representation 1002 can correspond to and/or represent an entity respiration signal such as, for instance, entity respiration signal 214 or entity respiration amplitude signal 418. Entity respiration signal representation 1002 can track (e.g., mimic, simulate, replicate, etc.) such an entity respiration signal in real-time (e.g., live, concurrently, and/or simultaneously with the entity's respiration). Suggested respiration signal representation 1004 can correspond to and/or represent a suggested respiration signal such as, for instance, suggested respiration signal 502. Suggested respiration signal representation 1004 can track (e.g., mimic, simulate, replicate, etc.) such a suggested respiration signal in real-time (e.g., live, concurrently, and/or simultaneously with the suggested respiration signal).

In the example embodiment depicted in FIG. 10A, alignment feedback data 1000*a* indicates that an entity respiration signal corresponding to entity respiration signal representation 1002 (e.g., entity respiration signal 214 or entity respiration amplitude signal 418) has a relatively poor alignment with a suggested respiration signal corresponding to suggested respiration signal representation 1004 (e.g., suggested respiration signal 502), as indicated by the relatively poor alignment of entity respiration signal representation 1002 with suggested respiration signal representation 1004. In the example embodiment depicted in FIG. 10B, alignment feedback data 1000*b* indicates that an entity respiration signal corresponding to entity respiration signal representation 1002 (e.g., entity respiration signal 214 or entity respiration amplitude signal 418) has a relatively good alignment with a suggested respiration signal corresponding to suggested respiration signal representation 1004 (e.g., suggested respiration signal 502), as indicated by the relatively good alignment of entity respiration signal representation 1002 with suggested respiration signal representation 1004.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure covers such alterations, variations, and equivalents.

What is claimed is:

1. A computing system, comprising:

one or more processors; and one or more non-transitory computer-readable storage media that store instructions that, when executed by the one or more processors, cause the computing system to perform operations, the operations comprising:

receiving input data comprising radar data indicative of an entity's respiration;

converting the radar data into an entity respiration signal by extracting phase data from the radar data and performing a signal phase unwrapping process on the phase data such that the entity respiration signal tracks the entity's respiration in real-time;

comparing the entity respiration signal to a suggested respiration signal indicative of a suggested respiration; and providing alignment feedback data to the entity in real-time based at least in part on the entity's respiration, the alignment feedback data comprising an alignment visualization of the entity respiration signal aligned with the suggested respiration signal.

2. The computing system of claim 1, wherein the operations further comprise:

determining an alignment score indicative of a degree of the alignment of the entity respiration signal with the suggested respiration signal.

3. The computing system of claim 1, wherein the alignment feedback data comprises an alignment score indicative of a degree of the alignment of the entity respiration signal with the suggested respiration signal.

4. The computing system of claim 1, wherein the alignment feedback data comprises an alignment visualization comprising at least one of the entity respiration signal or the suggested respiration signal.

5. The computing system of claim 1, wherein at least one of the input data or the radar data comprises at least one of radar data indicative of the entity's respiration, high frequency radar data indicative of the entity's respiration, sonar data indicative of the entity's respiration, sound data indicative of the entity's respiration, video data indicative of the entity's respiration, or time series data indicative of the entity's respiration.

6. A computer-implemented method, comprising:

receiving, by a computing system operatively coupled to one or more processors, input data comprising radar data indicative of an entity's respiration;

converting, by the computing system, the radar data into an entity respiration signal by extracting phase data from the radar data and performing a signal phase unwrapping process on the phase data such that the entity respiration signal tracks the entity's respiration in real-time;

comparing, by the computing system, the entity respiration signal to a suggested respiration signal indicative of a suggested respiration; and providing, by the computing system, alignment feedback data to the entity in real-time based at least in part on the entity's respiration, the alignment feedback data comprising an alignment visualization of the entity respiration signal aligned with the suggested respiration signal.

7. The computer-implemented method of claim 6, further comprising:

determining, by the computing system, an alignment score indicative of a degree of the alignment of the entity respiration signal with the suggested respiration signal.

8. The computer-implemented method of claim 6, wherein providing, by the computing system, the alignment feedback data to the entity in real-time based at least in part on the entity's respiration comprises:

providing, by the computing system, an alignment score indicative of a degree of the alignment of the entity respiration signal with the suggested respiration signal.

9. The computer-implemented method of claim 6, wherein providing, by the computing system, the alignment feedback data to the entity in real-time based at least in part on the entity's respiration comprises:

providing, by the computing system, an alignment visualization comprising at least one of the entity respiration signal or the suggested respiration signal.

10. The computer-implemented method of claim 6, wherein at least one of the input data or the radar data comprises at least one of radar data indicative of the entity's respiration, high frequency radar data indicative of the entity's respiration, sonar data indicative of the entity's respiration, sound data indicative of the entity's respiration, video data indicative of the entity's respiration, or time series data indicative of the entity's respiration.

11. A computing system, comprising:

one or more processors; and one or more non-transitory computer-readable storage media that store instructions that, when executed by the one or more processors, cause the computing system to perform operations, the operations comprising:

receiving a continuous chirp radar signal comprising radar data indicative of an entity's respiration, the continuous chirp radar signal comprising a plurality of chirps;

converting the continuous chirp radar signal into an entity respiration amplitude signal by extracting phase data from the radar data and performing a signal phase unwrapping process on the phase data such that the entity respiration amplitude signal tracks the entity's respiration in real-time, wherein signal amplitude of the entity respiration amplitude signal is generated upon receipt of each of the plurality of chirps;

comparing the entity respiration amplitude signal to a suggested respiration signal indicative of a suggested respiration; and providing alignment feedback data to the entity in real-time based at least in part on the entity's respiration, the alignment feedback data comprising an alignment visualization of the entity respiration amplitude signal aligned with the suggested respiration signal.

12. The computing system of claim 11, wherein the operations further comprise:

determining an alignment score indicative of a degree of the alignment of the entity respiration amplitude signal with the suggested respiration signal.

13. The computing system of claim 11, wherein the alignment feedback data comprises at least one of: an alignment score indicative of a degree of the alignment of the entity respiration amplitude signal with the suggested respiration signal; or an alignment visualization comprising at least one of the entity respiration amplitude signal or the suggested respiration signal.

14. The computing system of claim 11, wherein converting the continuous chirp radar signal into the entity respiration amplitude signal such that the entity respiration amplitude signal tracks the entity's respiration in real-time comprises:

removing noise data from the continuous chirp radar signal, the noise data comprising data indicative of at least one movement corresponding to one or more second entities.

15. The computing system of claim 14, wherein the operations further comprise:

mapping out a range associated with the continuous chirp radar signal, the range comprising at least a portion of the radar data.

16. The computing system of claim 15, wherein the operations further comprise:

normalizing the range into a range probability map comprising multiple range bins, the multiple range bins respectively comprising at least a portion of the radar data.

17. The computing system of claim 16, wherein the operations further comprise:

applying one or more inertia functions to at least one of the range probability map or the multiple range bins to determine a center-of-mass corresponding to at least one of the range probability map or the multiple range bins.

18. The computing system of claim 17, wherein the operations further comprise:

extracting phase data corresponding to the center-of-mass, the phase data being indicative of a wrapped phase signal corresponding to the center-of-mass.

19. The computing system of claim 18, wherein the operations further comprise:

performing a signal phase unwrapping process on at least one of the phase data or the wrapped phase signal to obtain a continuous phase signal corresponding to the center-of-mass.

20. The computing system of claim 19, wherein the operations further comprise:

applying a filter to the continuous phase signal to obtain the entity respiration amplitude signal, the filter being operable to remove data indicative of defined entity movements associated with the entity's respiration.

* * * * *